United States Patent
Cormier et al.

(10) Patent No.: US 10,507,212 B2
(45) Date of Patent: *Dec. 17, 2019

(54) METHOD FOR USE OF HOMOPIPERAZINIUM COMPOUNDS IN THE TREATMENT OF CANCER

(71) Applicant: UNIVERSITÉ LAVAL, Québec (CA)

(72) Inventors: Yvon Cormier, Québec (CA); Evelyne Israel-Assayag, Québec (CA)

(73) Assignee: UNIVERSITÉ LAVAL, Québec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/921,138

(22) Filed: Mar. 14, 2018

(65) Prior Publication Data

US 2018/0235978 A1    Aug. 23, 2018

Related U.S. Application Data

(62) Division of application No. 15/301,523, filed as application No. PCT/CA2015/050262 on Apr. 1, 2015, now Pat. No. 9,949,984.

(60) Provisional application No. 61/974,681, filed on Apr. 3, 2014, provisional application No. 62/074,233, filed on Nov. 3, 2014.

(51) Int. Cl.
| | |
|---|---|
| *A61K 31/551* | (2006.01) |
| *A61K 31/435* | (2006.01) |
| *A61K 31/44* | (2006.01) |
| *C07D 243/08* | (2006.01) |
| *C07D 401/04* | (2006.01) |

(52) U.S. Cl.
CPC .......... *A61K 31/551* (2013.01); *A61K 31/435* (2013.01); *A61K 31/44* (2013.01); *C07D 243/08* (2013.01); *C07D 401/04* (2013.01)

(58) Field of Classification Search
CPC .... A61K 31/435; A61K 31/44; A61K 31/551; C07D 243/08; C07D 401/04
See application file for complete search history.

(56) References Cited

U.S. PATENT DOCUMENTS

2004/0132737 A1    7/2004 Cormier et al.

FOREIGN PATENT DOCUMENTS

CA    2 573 977 A1    1/2006

OTHER PUBLICATIONS

International Search Report (PCT/ISA/210) dated Jun. 15, 2015, by the Canadian Intellectual Property as the International Searching Authority for International Application No. PCT/CA2015/050262.
Written Opinion (PCT/ISA/237) dated Jun. 15, 2015, by the Canadian Intellectual Property Office as the International Searching Authority for International Application No. PCT/CA2015/050262.
Ambrosi, P. & Becchetti, A. "Targeting Neuronal Nicotinic Receptors in Cancer: New Ligands and Potential Side-Effects". Recent Patents on Anti-Cancer Drug Disc. vol. 8. 2013. pp. 38-52.
Assayag, E.I. et al. "Bronchodilatory and Anti-Inflammatory Effects of ASM-024, a Nicotinic Recpetor Ligand, Developed for the Treatment of Asthma". PLos ONE. vol. 9. 1. 2014. pp. 1-10.
Improgo, M.R. et al. "Nicotinic acetylcholine receptors mediate lung cancer growth". Frontiers in Physiology. vol. 4. Article 251. 2013. pp. 1-6.
Kikuchi, J. et al. "Homopiperazine Derivatives as a Novel Class of Proteasome Inhibitors with a Unique Mode of Proteasome Binding". PLos ONE. vol. 8. 4. 2013. pp. 1-11.
Teimoori, S. et al. "Synthesis and antiproliferative activity of novel homopiperazine derivatives in leukemia cells". Chemistry & Biology Interface. 1, 1. 2011. pp. 59-67.

*Primary Examiner* — Yong S. Chong
(74) *Attorney, Agent, or Firm* — Buchanan Ingersoll & Rooney P.C.

(57) ABSTRACT

A method for treating cancer including administering to a patient in need thereof an effective amount of a compound having the formula:

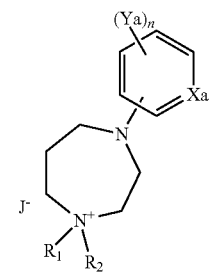

wherein $R_1$, $R_2$, Ya, Xa, and $J^-$ are as defined herein, and may be where R1 and R2 are independently selected from methyl, ethyl, n-propyl, or i-propyl; Xa is N or CH; Ya is hydrogen or independently selected from halogen, cyano, hydroxyl, alkyl of 1 to 6 carbon atoms, alkoxy of 1 to 6 carbon atoms, heteroaryl of 6 members and aryl; n is 1 or 2; wherein $J^-$ is fluoride, chloride, bromide, iodide, acetate, sulfate or sulfonate such as tosylate, mesylate, besylate.

14 Claims, 15 Drawing Sheets

N = 7, IC$_{50}$ = 33 ± 11 µM for Day 3; IC$_{50}$ = 52 ± 24 µM for Day 6

N=6, IC$_{50}$ = 210 ± 163 µM for Day 3; IC$_{50}$ = 288 ± 245 µM for Day 6

N=2 for Day 3 and N=4 for Day 6; IC50 = 172 ± 75 μM for Day 3; IC50 = 137 ± 92 μM for Day 6

METHOD FOR USE OF HOMOPIPERAZINIUM COMPOUNDS IN THE TREATMENT OF CANCER

CROSS REFERENCE TO RELATED APPLICATIONS

The present application is a divisional of U.S. application Ser. No. 15/301,523, filed on Oct. 3, 2016, which is a U.S. national stage of international Application No. PCT/CA2015/050262, filed on Apr. 1, 2015, which claims the benefit of U.S. Provisional Application No. 62/074,233, filed on Nov. 3, 2014 and the benefit of U.S. Provisional Application No. 61/974,681, filed on Apr. 3, 2014. The entire contents of each of U.S. application Ser. No. 15/301,523, International Application No. PCT/CA2015/050262, U.S. Provisional Application No. 62/074,233, and U.S. Provisional Application No. 61/974,681 are hereby incorporated herein by reference in their entirety.

FIELD OF THE DISCLOSURE

The present disclosure relates to novel use and method for the treatment or prevention for treating or preventing cancer or for reducing or stopping the proliferation of cancer cells.

BACKGROUND OF THE DISCLOSURE

A broad group of diseases involving unregulated cell growth is known as cancer or as malignant neoplasia. In cancer, cells divide and grow uncontrollably, causing the cells to form lumps or tumors. The cancer may also spread to more distant parts of the body through the lymphatic system or bloodstream. Not all tumors are cancerous; benign tumors do not invade neighboring tissues and do not spread throughout the body.

For the treatment of cancer, chemotherapeutic, immunotherapeutic or immunomodulatory and antiangiogenic agents have been reported. Agents can be used as monotherapy (treatment with one agent) or as combination therapy (simultaneous, separate or sequential treatment with another agent). The treatments may also be combined with radiotherapy.

In this respect, a chemotherapeutic agent means a naturally occurring, semi-synthetic or synthetic chemical compound which, alone or via further activation, for example with radiations in the case of radio-immunotherapy, inhibits or kills growing cells, and which can be used or is approved for use in the treatment of diseases of oncological nature, which are commonly also denominated as cancers. In the literature, these agents are generally classified according to their mechanism of action. In this matter, reference can be made, for example, to the classification made in "Cancer Chemotherapeutic Agents", American Chemical Society, 1995, W.O. Foye Ed.

Even if several therapeutic agents have already been investigated and used, there is still a need for new and efficient therapeutic agents for the treatment of cancer diseases.

One object of the present invention is to provide a method for the treatment of various cancer diseases.

SUMMARY

In one aspect, there is provided a method, composition or use for treating or preventing cancer, comprising administering an effective amount of a compound having the formula:

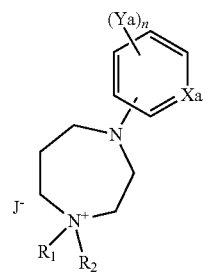

In one aspect, there is provided a combination for treating or preventing cancer comprising a compound as defined herein and an additional anticancer drug.

In one aspect, there is provided a method, composition or use for reducing or stopping the proliferation of cancer cells.

In one aspect, there is provided a combination for reducing or stopping the proliferation of cancer cells and an additional drug useful for reducing or stopping the proliferation of cancer cells.

In one aspect, there is provided a pharmaceutical composition comprising an effective amount of a compound as defined herein and a pharmaceutically acceptable carrier or excipient.

In one aspect, there is provided a pharmaceutical composition comprising an effective amount of a compound as defined herein and optionally one or more agents for treating or preventing cancer or for reducing or stopping the proliferation of cancer cells.

DESCRIPTION OF THE EMBODIMENTS

Figure 1A:
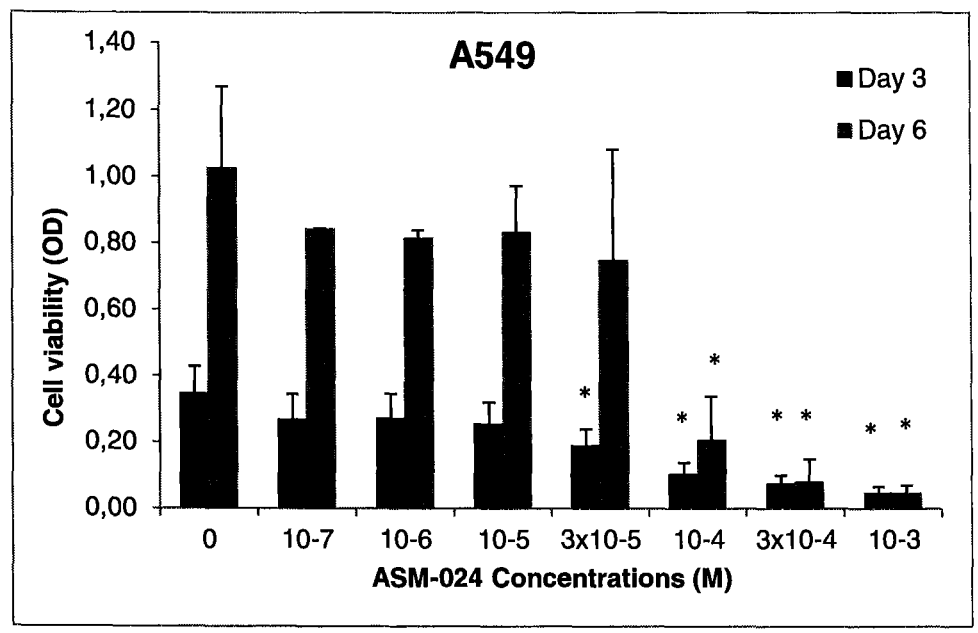
FIGS. 1A-1C show compound-induced dose-related inhibition of A549, H520 and H82 cell proliferation.

In one embodiment, Xa is CH. In one embodiment, Xa is N

In one embodiment, Ya is hydrogen or independently selected from halogen, amino, amidino, amido, azido, cyano, guanido, hydroxyl, nitro, nitroso, urea, sulfate, sulfite, sulfonate, sulphonamide, phosphate, phosphonate, acyl, acyloxy, alkyl of 1 to 6 carbon atoms, alkoxy of 1 to 6 carbon atoms, alkylthio of 1 to 6 carbon atoms, alkylamino of 1 to 6 carbon atoms, alkanol of 1 to 6 carbon atoms, aralkyl, aryl of 6 to 10 carbon atoms and 3 to 10 membered heterocycle.

In one embodiment, Ya is hydrogen or independently selected from halogen, amino, amidino, cyano, hydroxyl, nitro, urea, sulfate, sulfite, sulfonate, phosphate, phosphonate, acyl, acyloxy, alkyl of 1 to 6 carbon atoms, alkoxy of 1 to 6 carbon atoms, alkylthio of 1 to 6 carbon atoms, alkylamino of 1 to 6 carbon atoms, and alkanol of 1 to 6 carbon atoms; aryl and heteroaryl.

In one embodiment, Ya is hydrogen or independently selected from halogen, cyano, hydroxyl, alkyl of 1 to 6 carbon atoms, alkoxy of 1 to 6 carbon atoms, heteroaryl of 6 members and aryl. In one embodiment, Ya is hydrogen or independently selected from halogen, cyano, hydroxyl, alkyl of 1 to 6 carbon atoms, alkoxy of 1 to 6 carbon atoms and heteroaryl of 6 members and aryl of 6 or 10 carbon atoms.

In one embodiment, the homopiperazinium compound is a compound wherein $J^-$ is a halogen, a sulphate, acetate or a sulfonate. In one embodiment, the homopiperazinium compound is a compound wherein $J^-$ is a halogen or a sulfonate.

In one embodiment, the homopiperazinium compound is a compound wherein $J^-$ is a halogen.

In one embodiment, the halogen is iodide, chloride or bromide. In one embodiment, the halogen is iodide. In one embodiment, the halogen is chloride. In one embodiment, the halogen is bromide.

In one embodiment, the homopiperazinium compound is a compound wherein $J^-$ is a sulfonate. In one embodiment, the sulfonate is 4-toluenesulfonate, phenylsulfonate or methanesulfonate. In one embodiment, the sulfonate is 4-toluenesulfonate. In one embodiment, the sulfonate is phenylsulfonate. In one embodiment, the sulfonate is methanesulfonate.

In one embodiment, n is 1 to 4. In one embodiment, n is 1 to 3. In one embodiment, n is 1 or 2.

In one embodiment, $R_1$ and $R_2$ are independently selected from methyl, ethyl, n-propyl, or i-propyl;
Xa is CH;
Ya is hydrogen.

In one embodiment, R1 and R2 are independently selected from methyl, ethyl, n-propyl, or i-propyl;
Xa is N or CH;
Ya is hydrogen or independently selected from halogen, cyano, hydroxyl, alkyl of 1 to 6 carbon atoms, alkoxy of 1 to 6 carbon atoms, heteroaryl of 6 members and aryl;
n is 1 or 2;
wherein $J^-$ is fluoride, chloride, bromide, iodide, acetate, sulfate or sulfonate such as tosylate, mesylate, besylate.

In one embodiment, R1 and R2 are independently selected from methyl, ethyl, n-propyl, or i-propyl;
Xa is N or CH;
Ya is hydrogen or independently selected from halogen, cyano, hydroxyl, alkyl of 1 to 6 carbon atoms, alkoxy of 1 to 6 carbon atoms, heteroaryl of 6 members and aryl;
n is 1;
wherein $J^-$ is fluoride, chloride, bromide, iodide, acetate, sulfate or sulfonate such as tosylate, mesylate, besylate.

In one embodiment, R1 and R2 are independently selected from methyl, ethyl, n-propyl, or i-propyl;
Xa is N;
Ya is hydrogen or independently selected from halogen, cyano, hydroxyl, alkyl of 1 to 6 carbon atoms, alkoxy of 1 to 6 carbon atoms, heteroaryl of 6 members and aryl;
n is 1;
wherein $J^-$ is fluoride, chloride, bromide, iodide, acetate, sulfate or sulfonate such as tosylate, mesylate, besylate.

In one embodiment, R1 and R2 are independently selected from methyl, ethyl, n-propyl, or i-propyl;
Xa is CH;
Ya is hydrogen or independently selected from halogen, cyano, hydroxyl, alkyl of 1 to 6 carbon atoms, alkoxy of 1 to 6 carbon atoms, heteroaryl of 6 members and aryl;
n is 1;
wherein $J^-$ is fluoride, chloride, bromide, iodide, acetate, sulfate or sulfonate such as tosylate, mesylate, besylate.

In one embodiment, R1 and R2 are independently selected from methyl, ethyl, n-propyl, or i-propyl;
Xa is CH;
Ya is hydrogen
n is 1
wherein $J^-$ is fluoride, chloride, bromide, iodide, sulfate or sulfonate.

In one embodiment, R1 and R2 are independently selected from methyl, ethyl, n-propyl, or i-propyl;
Xa is CH;
Ya is hydrogen
n is 1
wherein $J^-$ is sulfonate.

In one embodiment, R1 and R2 are ethyl;
Xa is CH;
Ya is hydrogen
n is 1
wherein $J^-$ is tosylate.

The term "alkyl" represents a linear or branched hydrocarbon moiety having 1 to 10 or preferably 1 to 6 carbon atoms, which may have one or more unsaturation in the chain, and is optionally substituted. The term "lower alkyl" is also meant to include alkyls in which one or more hydrogen atom is replaced by a halogen, ie. an alkylhalide.

The term "cycloalkyl" represents an alkyl chain of 3 to 6 carbon atoms.

The term "alkoxy" represents an alkyl which is covalently bonded to the adjacent atom through an oxygen atom.

The term "alkylthio" represents an alkyl which is covalently bonded to the adjacent atom through a sulfur atom.

The term "alkylamino" represents an alkyl which is covalently bonded to the adjacent atom through a nitrogen atom and may be monoalkylamino or dialkylamino, wherein the alkyl groups may be the same or different.

The term "alkanol" represents an "alkyl" moiety for which one of the hydrogens has been replaced by an hydroxyl group.

The term "aralkyl" represents an aryl group attached to the adjacent atom by a $C_{1-6}$ alkyl.

The term "aryl" represents a carbocyclic moiety containing at least one benzenoid-type ring (i.e. may be monocyclic or polycyclic) having 6 to 10 carbon atoms, and which may be optionally substituted with one or more substituents. Alternatively, the ring may be containing 6 carbon atoms.

The term "acyl" is defined as a radical derived from a carboxylic acid, obtained by replacement of the —OH group. Like the acid to which it is related, an acyl radical may be derived form a straight chain, branched chain or cyclic alkyl or aryl.

The term "acyloxy" represents an acyl which is covalently bonded to the adjacent atom through an oxygen atom.

The term "halogen atom" is specifically a fluoride atom, chloride atom, bromide atom or iodide atom.

The term "heterocycle" represents a 3 to 10 membered optionally substituted saturated, unsaturated cyclic moiety wherein said cyclic moiety is interrupted by at least one heteroatom selected from oxygen (O), sulfur (S) or nitrogen (N). Alternatively, heterocycles may be 3 to 6 membered ring or 5 to 6 membered ring. Heterocycles may be monocyclic or polycyclic rings.

The term "heteroaryl" represents an aryl ring wherein said ring is interrupted by at least one heteroatom selected from oxygen (O), sulfur (S) or nitrogen (N). Preferably, heteroaryl rings may be containing 5 or 6 ring members.

The term "counterion" is meant to include a pharmaceutically acceptable ion that accompanies an ionic species (e.g. the homopiperazinium moiety) in order to maintain electric neutrality. Counterions can also be provided by the conjugate bases derived from pharmaceutically acceptable inorganic and organic acids such as hydrochloric, hydrobromic, sulphuric, nitric, perchloric, fumaric, maleic, phosphoric, glycollic, lactic, salicylic, succinic, paratoluene-sulphonic, tartaric, acetic, trifluoroacetic, citric, methanesulphonic, formic, benzoic, malonic, naphthalene 2 sulphonic and benzenesulphonic acids.

The term "independently" means that a substituent can be the same or a different definition for each item.

As used herein, "treatment" or "treating" refers to at least i) controlling or ameliorating at least one disease described herein, at least for the duration of said treatment.

Although not limited to such patients, "prevention" or "prophylaxis" treatment (which may be used interchangeably) is expected to be particularly useful to the treatment of patients who have suffered a previous episode associated with diseases described herein, or are otherwise considered to be at increased risk of said diseases. A successful preventive treatment would normally be expected to i) reduce the occurrences of a further episode, ii) reduce its severity or iii) prevent occurrences of further episodes, at least for the duration of the therapy.

In one embodiment, the present disclosure provides a method, use or composition for treating cancer comprising administering an effective amount of at least one compound as defined herein.

In one embodiment, the present disclosure provides a method, use or composition for limiting, or inhibiting the proliferation of cancer cells, or for causing death of cancer cells in a patient, comprising administering an effective amount of at least one compound as defined herein.

In another embodiment, the expression "cancer" includes, but is not limited to carcinomas, sarcomas, melanomas; lymphoma, leukemia and myelomas; blastomas; germ cell tumor; glioma and other CNS cancers.

In one embodiment, the carcinoma is a cancer of the bladder, breast, cervix, colon, esophagus, kidney, liver, larynx, lung (small and non-small cell lung cancer), oral cavity, ovary, pancreas, pleura, prostate, skin (basal and squamous), stomach, thyroid or uterus.

In one embodiment, the sarcoma is osteosarcoma, chondrosarcoma, liposarcoma, neurosarcoma, rhabdomyosarcoma, Erwing sarcoma or fibrosarcoma.

In one embodiment, the melanoma is malignant melanoma, lentigo maligna melanoma, superficial spreading melanoma, acral lentiginous melanoma, mucosal melanoma, nodular melanoma, polypoid melanoma, desmoplastic melanoma, amelanotic melanoma or soft-tissue melanoma.

In one embodiment, the lymphoma, leukemia and myelomas is acute lymphocytic leukemia, B-cell lymphoma, Burketts lymphoma, Hodgkin and Non-Hodgkin lymphoma, acute and chronic myelogenous leukemias, promyelocytic leukemia or multiple myeloma.

In one embodiment, the blastoma is a blastoma derived from immature "precursor" cells or embryonic tissue, neuroblastoma, retinoblastoma, pleuropulmonary blastoma, nephroblastoma (Wilms tumor) or hepatoblastoma.

In one embodiment, the germ cell tumor is a seminoma, dysgerminoma or teratocarcinoma tumor.

In one embodiment, the glioma and other CNS cancers are ependymomas, astrocytomas, oligodendrogliomas, glioblastomas or oligoastrocytomas.

In a further embodiment the invention relates to a method, use or composition for the treatment of cell proliferation, migration or apoptosis of cancer cells, or angiogenesis, in a human or non-human mammalian body.

In a further embodiment the invention relates to a method, use or composition for reducing or stopping the proliferation of cancer cells. By proliferation it is meant cell proliferation resulting from unregulated and/or undesirable cell growth, for example caused by excessive cell division, cell division at an accelerated rate and/or undesirable cell survival.

In another embodiment, the present disclosure provides a combination comprising a therapeutically effective amount of a compound, as defined herein, and a therapeutically effective amount of at least one or more therapeutic agents useful in the method of the present disclosure selected from: Alkylating agents, Anti-metabolites, Plant alkaloids and terpenoids, Vinca alkaloids, Podophyllotoxin, Taxanes, Topoisomerase inhibitors, and Cytotoxic antibiotics In another embodiment, the present invention provides a combination comprising a therapeutically effective amount of a compound, as defined herein, and a therapeutically effective amount of at least one or more therapeutic agents useful in the method of the present disclosure including but not limited to imatinib, paclitaxel, docetaxel, cisplatin, doxorubicine, vinblastine, zoledronate and/or in conjunction with antimetastatic agents, antiangionevic agents such as avastatin, and antiapoptotic compounds such as Velcade™, agents targeting synthesis of estrogens or estrogen signaling through estrogen receptors including but not limited to arimidex and tamoxifen, agents targeting biosynthesis of androgens or androgen signaling through the androgen receptor including but not limited to bicalutamide, agents targeting HER2 including but not limited to trastuzumab, agents targeting BRAF including but not limited to Vemurafenib, or agents targeting members of the MAP kinase family or their upstream or downstream effector kinases.

It will be clear to a person of ordinary skill that the amounts and/or ratios of therapeutic agents will be readily adjusted. It will be understood that the scope of combinations described herein is not particularly limited, but includes in principle any therapeutic agent useful for preventing or treating the diseases described herein.

It will also be appreciated that the amounts and/or ratios of therapeutic agents for use in treatment will vary not only with the particular agent selected but also with the route of administration, the nature of the condition for which treatment is required and the age and condition of the patient and will be ultimately at the discretion of the attendant physician.

The homopiperazinium compounds defined herein can be administered concurrently to the one or more agents used herein in the methods and combinations. The desired doses may conveniently be presented in a single dose or as divided dose administered at appropriate intervals, for example as two, three, four or more doses per day or continuously such as in a perfusion. The compound can be administered on a dosage regimen distinct to the one or more agents used herein in the methods and combinations. Alternatively, the compound can be administered sequentially or concurrently in distinct formulations or in a common formulation.

Pharmaceutical compositions may comprise pharmaceutically acceptable carriers.

The formulations may, where appropriate, be conveniently presented in discrete dosage units and may be prepared by any of the methods well known in the art of pharmacy. All methods include the step of bringing into association the active compound with a liquid carrier or solid carrier or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds and combinations according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

The following examples are provided to further illustrate details for the preparation and use of the compounds of the present invention. They are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus.

General Experimental Methods

Reactions were performed under argon atmosphere. Melting points are uncorrected. $^1$H NMR spectra were recorded at 400 MHz and were referenced to the peak for residual solvent. $^{13}$C NMR spectra were recorded at 100 MHz ($^{13}$C NMR at 75 MHz for Preparative Example) and were referenced to the peak for residual solvent. Chemical shifts in $^1$H and $^{13}$C NMR spectra are reported in ppm. All reagents (e.g. 1-methylhomopiperazine and homopiperazine) can be obtained commercially, e.g. from Sigma-Aldrich Co. Usual solvents and chemicals can be obtained commercially, e.g. from VWR, A&C or Fisher and were also "reagent" grade. Chromatography was performed using Silica Gel 60 (Merck; 230-400 mesh). Accurate mass measurements were performed on a LC-MSD-Tof instrument from Agilent technologies in positive electrospray mode. Protonated molecular ions (M+H)$^+$ was used for empirical formula confirmation.

PREPARATIVE EXAMPLE 1

1-Phenyl-4-ethyl-homopiperazine

RP-HPLC conditions (Preparative Example):

HPLC analysis were performed on a Waters C18 reversed-phase analytical column (5 µm, Atlantis, 100×3.9 mm) using a flow rate of 1 mL/min and a gradient of 0% to 95% A/B over 15 min, where A=0.1% aqueous Formic Acid and B=CH$_3$CN+0.1% FA A solution of homopiperazine (50 g, 499.1 mmol, 1.2 eq), iodobenzene (84.86 g, 416 mmol, 1 eq), ethylene glycol (46.4 mL, 832 mmol, 2 eq), CuI (3.96 g, 20.8 mmol, 5% mol) and K$_3$PO$_4$ (88.3 g, 416 mmol, 1 eq) and isopropanol (416 mL) was stirred at reflux for 46 h. The resulting mixture was cooled down to room temperature and isopropanol was evaporated. Water (200 mL), containing NH$_4$OH (1%), and EtOAc (250 mL) were added to the mixture. The aqueous layer was extracted with EtOAc (4×200 mL), and the combined organic layers were washed with brine (2×200 mL), dried over Na$_2$SO$_4$, filtered and evaporated. The crude product (52.2 g) was obtained as a brown oil and was used in the next step without any purification.

To a solution of 1-phenylhomopiperazine (52.2 g, 292.6 mmol, 1 eq) in dichloromethane (300 mL) were added at 0° C. Et$_3$N (90 mL, 890 mmol, 3 eq) and Ac$_2$O (112.15 mL, 1186 mmol, 4 eq). The mixture was stirred at room temperature for 2 h. A 4N NaOH solution (200 mL) was added and the resulting mixture was extracted with CH$_2$Cl$_2$ (3×150 mL). The combined organic layers were washed with brine (2×150 mL), dried over Na$_2$SO$_4$ and evaporated. The resulting oil was coevaporated with EtOH (3×), EtOAc (3×) and Et$_2$O (3×), to give 68.03 g of crude product which was used in the next step without any purification.

To a suspension of AlLiH$_4$ (28.46 g, 750 mmol, 1.5 eq) in THF (400 mL) at 0° C. was added dropwise a solution of 1-phenyl-4-acyl-homopiperazine (109 g, 500 mmol, 1 eq) in THF (500 mL). The mixture was warmed up to room temperature and stirred for 24 h. The mixture was then cooled down to 0° C. and H$_2$O (350 mL) was added dropwise. THF was evaporated, TBME (400 mL) was added and the mixture was filtered on Celite ®. The layers were separated, and the aqueous phase was extracted with TBME (3×150 mL). The organic layers were combined and washed with brine (2×150 mL), dried over Na$_2$SO$_4$, filtered and evaporated. The crude product was purified by chromatography on silica gel using 100% hexanes and a gradient of 0% to 20% MeOH in CH$_2$Cl$_2$. The desired compound 1-Phenyl-4-ethyl-homopiperazine was obtained as a orange oil (38.1 g, 19% overall yield): $^1$H NMR CDCl$_3$ (ppm): 7.26 (dd, 2H), 6.73 (m, 3H), 3.61(t, 2H), 3.53 (t, 2H), 2.81 (m, 2H), 2.62 (m, 4H), 2.03 (m, 2H), 1.12 (t, 3H); $^{13}$C NMR CDCl$_3$ (ppm): 148.8, 128.9, 115.4, 111.2, 54.7, 53.8, 51.3, 48.3, 47.6, 27.4, 12.1.

PREPARATIVE EXAMPLE 2

1-methyl-4-phenylhomopiperazine

In a flame-dried round bottom flask under nitrogen, iodobenzene (1 eq, 1.47 mmol), N-methylhomopiperazine (1.2 eq, 1.76 mmol), ethylene glycol (2 eq, 2.94 mmol), CuI (5% mol) and K3PO4 (2 eq, 2.94 mmol) were suspended in isopropanol (3 ml). The mixture was refluxed with stirring for 17 hours. The resulting mixture was cooled down to room temperature and water was added (5 ml). The mixture was extracted with ether(4×10 ml) and the combined organic extracts washed with brine, dried over Na2SO4 and evaporated to dryness under vacuum. The crude product was purified using silica gel flash chromatography using a gradient of 0% a 7.5% (2M NH3)MeOH in chloroform. The desired product was obtained as a yellow oil. (yield 64%).

PREPARATIVE EXAMPLE 3

4-Methyl-1-(4-methoxyphenyl)-homopiperazine

To a solution of 1-methylhomopiperazine (918 mg, 8.04 mmol) in i-PrOH (10 mL) and ethylene glycol (0.90 mL) was added CuI (76 mg, 0.4 mmol), $K_3PO_4$ (1.706 g, 8.04 mmol) and 1-iodoanisole (1.882 g, 8.04 mmol). The reaction mixture was stirred under reflux for 48 h. After cooling, the mixture was taken in EtOAc and 0.5% aqueous $NH_4OH$. The layers were separated and the aqueous layer was extracted 3 times with EtOAc. The organic layers were combined, washed with brine, dried ($Na_2SO_4$) and concentrated to a residue that was purified by column chromatography on silica gel (5/95/0 to 19.9/80/0.1 MeOH/DCM/$NH_4OH$). Evaporation of the collected fractions yielded the title compound as a beige solid (711 mg, 40% yield). $^1$H NMR (400 MHz, $CDCl_3$) δ 6.83 (d, 2H), 6.64 (d, 2H), 3.74 (s, 3H), 3.53 (t, 2H), 3.43 (t, 2H), 2.71 (t, 2H), 2.59 (t, 2H), 2.39 (s, 3H), 2.01 (quad, 2H); HPLC: condition A, 4.67 min, >99% homogeneity; ES-MS [M+H$^+$]=221.2.

PREPARATIVE EXAMPLE 4

4-Methyl-1-(2,4-dimethoxyphenyl)-homopiperazine

To a solution of 1-methylhomopiperazine (1.377 g, 11.98 mmol) in i-PrOH (15 mL) and ethylene glycol (1.35 mL) was added CuI (114 mg, 0.60 mmol), $K_3PO_4$ (2.540 g, 11.98 mmol) and 1-iodo-2,4-dimethoxybeznene (3.160 g, 11.98 mmol). The reaction mixture was stirred under reflux for 7 days. After cooling, the mixture was taken in EtOAc and 0.5% aqueous $NH_4OH$. The layers were separated and the aqueous layer was extracted 3 times with EtOAc. The organic layers were combined, washed with brine, dried ($Na_2SO_4$) and concentrated to a residue that was purified by column chromatography on silica gel (5/95/0 to 19.9/80/0.1 MeOH/DCM/$NH_4OH$). Evaporation of the collected fractions yielded the title compound as a brown oil (614 mg, 20% yield). $^1$H NMR (400 MHz, $CDCl_3$) δ 6.88 (d, 1H), 6.45 (s, 1H), 6.38 (d, 1H), 3.81 (s, 3H), 3.76 (s, 3H), 3.25 (m, 4H), 2.75 (m, 4H), 2.40 (s, 3H), 1.96 (quad, 2H); HPLC: condition A, RT=4.80 min, 95.3% homogeneity.

PREPARATIVE EXAMPLE 5

4-Methyl-1-(4-trifluoromethylphenyl)-homopiperazine

To a solution of 1-methylhomopiperazine (1.193 g, 10.45 mmol) in i-PrOH (10 mL) and ethylene glycol (1.16 mL) was added CuI (100 mg, 0.52 mmol), $K_3PO_4$ (2.218 g, 10.45 mmol) and 4-iodobenzotrifluoride (2.842 g, 10.45 mmol). The reaction mixture was stirred under reflux for 24 h. After cooling, the mixture was taken in EtOAc and 0.5% aqueous $NH_4OH$. The layers were separated and the aqueous layer was extracted 3 times with EtOAc. The organic layers were combined, washed with brine, dried ($Na_2SO_4$) and concentrated to a residue which was purified by column chromatography on silica gel (2/95/0 to 9.9/90/0.1 MeOH/DCM/$NH_4OH$). Evaporation of the collected fractions yielded the title compound as a colorless oil (713 mg, 26% yield). $^1$H NMR (400 MHz, $CDCl_3$) δ 7.41 (d, 2H), 6.68 (d, 2H), 3.60 (m, 2H), 3.51 (m, 2H), 2.71 (m, 2H), 2.56 (m, 2H), 2.38 (s, 3H), 2.02 (quad, 2H); HPLC: condition A, RT=5.20 min, 98.7% homogeneity.

PREPARATIVE EXAMPLE 6

4-Methyl-1-(4-trifluorobenzyl)-homopiperazine

At 100° C., 1-methylhomopiperazine (1.22 g, 10.68 mmol) was allowed to react with 4-bromobenzotrifluoride (2 g, 8.9 mmol) using catalytic amount of $Pd_2(dba)_3$ (82 mg, 0.089 mmol) and BINAP (166 mg, 0.267 mmol), NaOtBu (1.2 g, 12.46 mmol) with without solvent (neat). The reaction mixture was stirred under reflux for 1 h15. After cooling, the mixture was taken in DCM and $H_2O$. The layers were separated and the aqueous layer was extracted 3 times with DCM. The organic layers were combined, dried ($Na_2SO_4$) and concentrated to a residue which was purified by column chromatography on silica gel (4.9/95/0.1 MeOH/DCM/$NH_4OH$). Evaporation of the collected fractions yielded the title compound as a brown oil (1.64 g, 72% yield). $^1$H NMR (400 MHz, $CDCl_3$) δ 7.42 (d, 2H), 6.98 (d, 2H), 3.59 (t, 2H), 3.50 (t, 2H), 2.69 (m, 2H), 2.54 (m, 2H), 2.38 (s, 3H), 2.01 (m, 2H); $^{13}$C NMR ($CDCl_3$) δ 27.1, 46.3, 47.7, 48.0, 56.6, 57.3, 110.3, 116.2, 116.5, 116.8, 117.1, 123.5, 126.0, 126.1, 126.2, 150.9; MS (+) 259.2; HPLC: condition A, RT=5.38 min, >98% homogeneity.

PREPARATIVE EXAMPLE 7

4-Methyl-1-(4-cyanophenyl)-homopiperazine

To a solution of 1-methylhomopiperazine (955 mg, 8.36 mmol) in THF (17 mL) was added $Pd_2(dba)_3$ (957 mg, 1.05 mmol), BINAP (1.302 g, 2.09 mmol), NaOt-Bu (938 mg, 9.76 mmol) and 4-iodobenzonitrile (1.596 g, 6.97 mmol). The reaction mixture was stirred under reflux for 1 h. After cooling, the mixture was diluted with $Et_2O$ (200 mL), filtered and evaporated. The crude product was purified by column chromatography on silica gel (0/95/0 to 14.9/85/0.1 MeOH/DCM/$NH_4OH$). Evaporation of the collected fractions yielded the title compound as a beige solid (915 mg, 61% yield). $^1$H NMR (400 MHz, $CDCl_3$) δ 7.44 (d, 2H), 6.63 (d, 2H), 3.59 (t, 2H), 3.49 (t, 2H), 2.69 (m, 2H), 2.55 (m, 2H), 2.37 (s, 3H), 2.00 (quad, 2H); HPLC: condition A, RT=4.48 min, 95.0% homogeneity.

PREPARATIVE EXAMPLE 8

4-Methyl-1-(3-methylphenyl)-homopiperazine

At 100° C., 1-methylhomopiperazine (1.6 g, 14 mmol) was allowed to react with 3-bromotoluene (2 g, 11.7 mmol) using catalytic amount of $Pd_2(dba)_3$ (107 mg, 0.1169 mmol) and BINAP (218 mg, 0.35 mmol), NaOtBu (1.6 g, 16.37 mmol) with without solvent (neat). The reaction mixture was stirred under reflux for 4 h. After cooling, the mixture was taken in DCM and $H_2O$. The layers were separated and the aqueous layer was extracted 3 times with DCM. The organic layers were combined, dried (Na$_2$SO$_4$) and concentrated to a residue which was purified by column chromatography on silica gel (4.9/95/0.1 MeOH/DCM/NH$_4$OH).

Evaporation of the collected fractions yielded the title compound as a brown oil (1.28 g, 54% yield). $^1$H NMR (400 MHz, CDCl$_3$) δ 7.16 (t, 1H), 6.56 (m, 3H), 3.61 (m, 2H), 3.52 (m, 2H), 2.74 (m, 2H), 2.61 (m, 2H), 2.43 (s, 3H), 2.38 (s, 3H), 2.06 (m, 2H); $^{13}$C NMR (CDCl$_3$) δ 21.1, 27.5, 46.3, 47.9, 48.1, 56.8, 57.9, 108.4, 111.9, 116.4, 128.8, 138.5, 149.0; MS (+) 205.2; HPLC: condition A, RT=4.87 min, 100% homogeneity.

PREPARATIVE EXAMPLE 9

4-Methyl-1-(3,5-dimethoxyphenyl)-homopiperazine

At 100° C., 1-methylhomopiperazine (1.36 g, 11.88 mmol) was allowed to react with 1-bromo-3,5-dimethoxybenzene (2.15 g, 9.9 mmol) using catalytic amount of Pd$_2$(dba)$_3$ (90.65 mg, 0.099 mmol) and BINAP (185 mg, 0.297 mmol), NaOtBu (1.34 g, 13.86 mmol) with without solvent (neat). The reaction mixture was stirred under reflux for 23 h. After cooling, the mixture was taken in DCM and H$_2$O. The layers were separated and the aqueous layer was extracted 3 times with DCM. The organic layers were combined, dried (Na$_2$SO$_4$) and concentrated to a residue which was purified by column chromatography on silica gel (4.9/95/0.1 MeOH/DCM/NH$_4$OH). Evaporation of the collected fractions yielded the title compound as a brown oil (1.04 g, 46% yield). $^1$H NMR (400 MHz, CDCl$_3$) δ 5.86 (s, 3H), 3.77 (s, 6H), 3.52 (m, 2H), 3.44 (t, 2H), 2.66 (m, 2H), 2.53 (m, 2H), 2.36 (s, 3H), 1.98 (m, 2H); $^{13}$C NMR (CDCl$_3$) δ 27.4, 45.3, 48.0, 48.3, 54.8, 55.6, 57.7, 87.4, 90.6, 150.7, 161.3; MS (+) 251.2; HPLC: condition A, RT=4.85 min, 98% homogeneity.

PREPARATIVE EXAMPLE 10

1-(2-pyridyl)-homopiperazine

At 100° C., homopiperazine (3.82 g, 38.1 mmol) was allowed to react with 2-bromopyridine (2 g, 12.7 mmol) using catalytic amount of Pd$_2$(dba)$_3$ (116 mg, 0.127 mmol) and BINAP (237 mg, 0.381 mmol), NaOtBu (1.71 g, 17.78 mmol) with without solvent (neat). The reaction mixture was stirred under reflux for 1 h30. After cooling, the mixture was taken in DCM and H$_2$O. The layers were separated and the aqueous layer was extracted 3 times with DCM. The organic layers were combined, dried (Na$_2$SO$_4$) and concentrated to a residue which was purified by column chromatography on silica gel (9.9/90/0.1 to 14.9/85/0.1 MeOH/DCM/NH$_4$OH). Evaporation of the collected fractions yielded the title compound as a brown oil (1.23 g, 55% yield). The coupling was repeated with 3 g (19 mmol) of 2-bromopyridine to afford after purification 1.46 g of product (43% yield). $^1$H NMR (400 MHz, CDCl$_3$) δ 8.12 (m, 1H), 7.40 (m, 1H), 6.48 (m, 2H), 3.70 (m, 4H), 3.01 (m, 2H), 2.82 (m, 2H), 1.86 (m, 2H), 1.69 (s, 1H); MS (+) 178.0; HPLC: condition A, RT=1.50 min, 100% homogeneity.

PREPARATIVE EXAMPLE 11

4-Ethyl-1-(2-pyridyl)-homopiperazine

To a solution of 1-(2-pyridyl)-homopiperazine (2.43 g, 13.73 mmol) in t-BuOH (14 mL) was added iodoethane (2.35 g, 15.1 mmol) and Na$_2$CO$_3$ (2.91 g, 27.46 mmol). The reaction mixture was stirred under reflux for 24 h. After cooling, the mixture was taken in EtOAc and a saturated solution of NaHCO$_3$. The layers were separated and the organic layer was washed 4 times with a saturated solution of NaHCO$_3$ and once with brine, dried (Na$_2$SO$_4$) and concentrated to a residue which was purified by column chromatography on silica gel (4.9/95/0.1 to 9.9/90/0.1 MeOH/DCM/NH$_4$OH). Evaporation of the collected fractions yielded the title compound as a brown oil (1.97 g, 70% yield). $^1$H NMR (400 MHz, CDCl$_3$) δ 8.04 (m, 1H), 7.30 (m, 1H), 6.37 (m, 2H), 3.69 (m, 2H), 3.50 (m, 2H), 2.64 (m, 2H), 2.45 (m, 4H), 1.88 (m, 2H), 0.96 (t, 3H); $^{13}$C NMR (CDCl$_3$) δ 11.9, 27.2, 45.9, 46.0, 51.3, 54.1, 54.9, 104.9, 110.8, 136.7, 147.4, 157.8; MS (+) 206.0; HPLC: condition A, RT=1.70 min, >99% homogeneity.

RP-HPLC Conditions (Examples):

HPLC analysis were performed on a Waters C18 reversed-phase analytical column (5 μm, Atlantis, 100×3.9 mm) using a flow rate of 1 mL/min and a gradient of 0% to 95% A/B over 15 min (condition A) or on a Phenomenex CN reversed-phase analytical column (5 μm, Luna CN, 150×4.6 mm) with a flow rate of 0.5 mL/min and a gradient of 15% to 95% A/B over 30 min (condition B), where A=CH$_3$CN+ 0.1% formic acid+0.1% triethylamine and B=0.1% aqueous formic acid+0.1% triethylamine.

EXAMPLE 1

1-Methyl-1-propyl-4-phenyl-homopiperazinium Iodide (ASM-008)

To a solution of 1-phenyl-4-methylhomopiperazine (1.9 g, 10 mmol) in acetone (60 mL) was added 1-propyliodide (8.5 g, 50 mmol). The mixture was heated to reflux for 15 h, after which it became dark orange. After cooling, and evaporation of the solvent to give an orange oil which was purified by passing through a pad of silica gel and eluted using a mixture of 5% MeOH in DCM to give 2.307 g (89% yield) of the title compound as a yellow gum: Exact Mass Calcd for C$_{15}$H$_{25}$N$_2^+$ [M$^+$] 233.2012, found 233.2011.

1,1-dimethyl-4-phenylhomopiperazinium iodide (ASM-002) was prepared in a similar manner using methyl iodide (10eq.) and stirring at rt for 25 hours Yielding 66% of the compound. Melting point: 158-160. $^1$H NMR DMSO-d6 (ppm): (q, 2H) 7.18, (q, 2H) 6.74, (t, 1H) 6.64, (br s, 2H, 3.74), (m, 2H) 3.52, (m, 2H) 3.44, (t, 2H) 3.40, (s, 6H) 3.17, (bs s, 2H) 2.21. $^{13}$C NMR DMSO-d6: 149, 129, 117, 112, 66, 65, 53, 47, 43, 22.

EXAMPLE 2

1,1-Diethyl-4-phenyl-homopiperazinium Iodide (ASM-009)

To a solution of 1-phenyl-4-ethylhomopiperazine (14.87 g, 73 mmol) in acetone (75 mL) was added ethyliodide (22.74 g, 145.8 mmol). The mixture was heated to reflux for 22 h, cooled down to room temperature, and the resulting white solid was filtered under vacuum to afford 23.5 g (89% yield) of the title compound: mp=190.5-192.5° C.; $^1$H NMR D$_2$O (ppm): 7.31 (dd, 2H), 6.87 (m, 3H), 3.74(br s, 2H), 3.52 (m, 4H), 3.34 (m, 6H), 2.20 (br s, 2H), 1.26 (t, 6H); $^{13}$C NMR D$_2$O (ppm): 147.6, 129.4, 118.1, 113.1, 60.1, 59.6, 54.6, 46.5, 42.9, 21.5, 6.6; MS ES(+): (M−I$^-$)=233.2; 100% homogeneity (RT=13.94 min) by LC-MS using CN column with ACN—H$_2$O(0.1% formic acid) as eluent and UV detection at 240 nm.

EXAMPLE 3

1-Ethyl-1-n-propyl-4-phenyl-homopiperazinium Iodide (ASM-010)

To a solution of 1-phenyl-4-ethylhomopiperazine (1.6 g, 7.8 mmol) in acetone (50 mL) was added n-propyliodide (6.8 g, 40 mmol). The mixture was heated to reflux for 16 h, then allowed to cool to room temperature, and the solvent evaporated to dryness. The orange oily residue was purified by flash chromatography over silica gel using a gradient of 0-7% MeOH in DCM to afford 2.61 g (89% yield) of the title compound as a yellow thick oil: Exact Mass Calcd for $C_{16}H_{27}N_2^+$ [M$^+$] 247.2168, found 247.2173.

EXAMPLE 4

1,1-Dimethyl-4-(2-pyridyl)-homopiperazinium Iodide (ASM-016)

To a solution of 1-methyl-4-(2-pyridyl)-homopiperazine (1.1 g, 5.76 mmol) in a 1:1 mixture of acetone/Et$_2$O (20 mL) was added methyliodide (0.82 g, 5.8 mmol). After stirring at room temperature for 48 h, the solid formed was filtered, washed with 50 mL Et$_2$O and then dried 3 h under vacuum to afford 1.87 g (98% yield) of the title compound as a beige solid: LC-UV-MS analysis: 100% homogeneity (RT=13.49 min) using UV detection at 240 nm and CN column with ACN—H$_2$O (0.1% formic acid) as gradient eluent; Exact Mass Calcd for $C_{12}H_{20}N_3^+$ [M$^+$] 206.16517, found 206.16509; $^1$H NMR DMSO-d$_6$ (ppm): 8.10 (d, 1H), 7.55 (m, 1H), 6.69 (d, 1H), 6.63 (m, 1H), 4.03 (br s, 2H), 3.53 (m, 6H), 3.18 (s, 6H), 2.24 (br s, 2H); $^{13}$C NMR DMSO-d$_6$ (ppm): 22.1, 39.2, 45.7, 52.5, 64.8, 66.0, 106.5, 112.9, 138.2, 147.9, 157.9.

EXAMPLE 4

1-Ethyl-1-methyl-4-(2-pyridyl)-homopiperazinium Iodide (ASM-017)

To a solution of 1-methyl-4-(2-pyridyl)-homopiperazine (1.1 g, 5.76 mmol) in a 1:1 mixture of acetone/Et$_2$O (20 mL) was added ethyliodide (3.6 g, 23 mmol). The mixture was stirred at room temperature for 48 h, diluted with 20 mL of Et$_2$O and the solid was filtered, washed with Et$_2$O (30 mL), dried under vacuum to afford 1.89 g (95% yield) of the title compound as a beige powder: LC-UV-MS analysis: 100% homogeneity (RT=13.60 min) using UV detection at 240 nm and CN column with ACN—H$_2$O (0.1% formic acid) as gradient eluent; Exact Mass Calcd for $C_{13}H_{22}N_3^+$ [M$^+$] 220.18062, found 220.17991; $^1$H NMR DMSO-d$_6$ (ppm): 8.10 (d, 1H), 7.55 (m, 1H), 6.69 (d, 1H), 6.63 (m, 1H), 4.03 (m, 2H), 3.53 (m, 8H), 3.18 (s, 3H), 2.24 (m, 2H), 1.25 (t, 3H); $^{13}$C NMR DMSO-d$_6$ (ppm): 8.3, 21.9, 39.0, 45.6, 48.2, 59.3, 62.3, 63.9, 106.5, 112.9, 138.2, 147.9, 157.9.

EXAMPLE 5

1-Methyl-1-propyl-4-(2-pyridyl)-homopiperazinium Iodide (ASM-018)

To a solution of 1-methyl-4-(2-pyridyl)-homopiperazine (1.1 g, 5.76 mmol) in a 1:1 mixture of acetone/Et$_2$O (20 mL) was added propyliodide (3.9 g, 23 mmol). The mixture was stirred at room temperature for 72 h, diluted with 25 mL of Et$_2$O and the mixture was stirred for a further 24 h while a with solid was formed. Further dilution with Et$_2$O (25 mL), filtration and drying under vacuum afforded 1.69 g (81% yield) of the title compound as a beige solid: LC-UV-MS analysis: 100% homogeneity (RT=13.92 min) using UV detection at 240 nm and CN column with ACN—H$_2$O (0.1% formic acid) as gradient eluent; Exact Mass Calcd for $C_{14}H_{24}N_3^+$ [M$^+$] 234.19647, found 234.19618; $^1$H NMR DMSO-d$_6$ (ppm): 8.10 (d, 1H), 7.55 (m, 1H), 6.69 (d, 1H), 6.63 (m, 1H), 4.03 (br s, 2H), 3.50 (m, 8H), 3.18 (s, 3H), 2.24 (br s, 2H), 1.70 (m, 2H), 0.90 (t, 3H); $^{13}$C NMR DMSO-d$_6$ (ppm): 11.0, 15.8, 21.9, 39.0, 45.6, 49.1, 62.8, 64.5, 64.9, 106.5, 112.9, 138.2, 147.9, 157.9.

EXAMPLE 6

1,1-Diethyl-4-phenyl-homopiperazinium Bromide (ASM-021)

The resin Amberlite® IRA-400(Cl) (100 mL) was treated with 2N KBr (250 mL), and then washed with 200 mL H$_2$O. The compound ASM-009 (FG1-62, 2.286 g, 6.35 mmol) was dissolved in H$_2$O (50 mL) by heating slightly and put down on the resin. The product was eluted with water (500 mL) and the solvent was evaporated. The residue was analyzed by MS and a signal at m/e 127 was present. So, the resin was retreated with 2N KBr and the residue dissolved in 100 mL H$_2$O. By MS, always one signal at m/e 127. The resin was washed with deionized water and treated with 2N HBr (500 mL), washed with deionized water (350 mL), the residue dissolved in deionized water (100 mL) was passed through the resin. But by MS, 12.5% of I$^-$ were still present. So, a new resin was used: Amberlite® IRA-410(Cl) (100 mL), treated with 2N HBr (2×250 mL), washed with deionized water (250 mL). The residue was dissolved in deionized water (50 mL) and eluted from the resin with deionized water. After evaporation of the water, an oil was obtained and coevaporated with Et$_2$O/acetone to afford the title compound as a solid (1.616 g). The compound was dried by heating at 40° C. under vacuum for 24 h, but traces of acetone (5%) were detected by $^1$H NMR at 2.22 ppm. The product was analyzed by ES negative ion mode MS and signals at m/e 125 and 127 were present. But, these were adducts Br$^-$+HCO$_2$H (79+46=125; 81+46=127), because when acetic acid was used instead of formic acid, just two signals were present at m/e 79 and 81: $^1$H NMR D$_2$O (ppm): 7.38 (dd, 2H), 6.97 (m, 3H), 3.81 (br s, 2H), 3.56 (m, 4H), 3.41 (m, 6H), 2.24 (br s, 2H), 1.29 (t, 6H); MS ES(+): (M−Br$^-$)=233.2; 100% homogeneity (RT=14.21 min) by LC-MS using CN column with ACN—H$_2$O(0.1% formic acid) as eluent and UV detection at 240 nm.

EXAMPLE 7

1,1-Diethyl-4-phenyl-homopiperazinium Chloride (ASM-022)

The resin Amberlite® IRA-410(Cl) (100 mL) was treated with 2N HCl (250 mL), washed with 200 mL of distilled water. The compound ASM-009 (FG1-62, 2.84 g, 7.89 mmol) was dissolved in H$_2$O (60 mL) by heating slightly and put down on the column of resin. The product was eluted with water (500 mL) and the solvent was evaporated. The residue was triturated and coevaporated with Et$_2$O/acetone to afford the title compound as a solid (1.755 g). The compound was dried by heating at 40° C. under vacuum for 24 h, but traces of acetone (1%) were detected by $^1$H NMR at 2.22 ppm: mp=163.3-164.6° C.; $^1$H NMR D$_2$O (ppm):

7.34 (dd, 2H), 6.91 (m, 3H), 3.79 (br s, 2H), 3.56 (m, 4H), 3.46 (m, 6H), 2.24 (br s, 2H), 1.28 (t, 6H). By negative ES mode MS, Cl⁻ formed adducts with formic acid: m/e 35+46=81 and m/e 37+46=83; MS ES(+): (M−Cl⁻)=233.2; 100% homogeneity (RT=14.12 min) by LC-MS using CN column with ACN—$H_2O$(0.1% formic acid) as eluent and UV detection at 240 nm.

EXAMPLE 8

1,1-Diethyl-4-phenyl-homopiperazinium Acetate (ASM-023)

The resin Amberlite® IRA-410(Cl) (100 mL) was treated with 2N HBr (250 mL), washed with 250 mL of distilled water, treated with 2N NaOH (50 mL) in an ultrasonic bath for 10 minutes, washed with 2N NaOH (200 mL), treated with 2N AcOH (50 mL) in an ultrasonic bath for 20 minutes, washed with 2N AcOH (200 mL), and finally washed with water (250 mL). Compound ASM-009 (1.68 g, 4.67 mmol) was dissolved in $H_2O$ (60 mL) by heating slightly and eluted through the column of resin. By ES negative ion mode MS, the two signals corresponding to Br⁻ were present. Then the resin was retreated: 2N NaOH (100 mL) in an ultrasonic bath for 15 minutes, washed with 2 N NaOH (300 mL), washed with $H_2O$ (250 mL), treated with 2N AcOH (100 mL) in an ultrasonic bath for 25 minutes, washed with 2N AcOH (100 mL) and $H_2O$ (250 mL). The residue was dissolved in water (30 mL) and eluted through the column of resin with water. After evaporation, the title compound was obtained as an oil (1.40 g): ES negative mode MS: no signals for Br⁻ were detected; $^1$H NMR $D_2O$ (ppm): 7.21 (dd, 2H), 6.7 (m, 3H), 3.50 (br s, 2H), 3.30 (m, 4H), 3.15 (m, 6H), 2.01 (br s, 2H), 1.83 (s, 3H), 1.13 (t, 6H); MS ES(+): (M−AcO⁻)=233.2; 100% homogeneity (RT=11.95 min) by LC-MS using CN column with ACN—$H_2O$(0.1% formic acid) as eluent and UV detection at 240 nm.

EXAMPLE 9

1,1-Diethyl-4-phenyl-homopiperazinium Tosylate (ASM-024)

A 5 L three-necked flask, equipped with a mechanical stirrer and a condenser, is charged with 189.55 g (0.93 mol) of 1-phenyl-4-ethyl-homopiperazine and then 1 L of acetone. Ethyl p-toluenesulfonate (371.6 g, 1.86 mol, 2 equiv) plus 200 mL of acetone for wash then added and the mixture was heated gently to reflux temperature. After 4 h, crystals had started to form and 350 ml of acetone were added to facilitate the stirring. After 24 h, HPLC analysis indicated that there was some starting material left. Consequently, 1 additional equivalent of TsOEt was added (186 g) and the mixture was further heated to reflux. After a total of 94 h, HPLC analysis indicated that the reaction had not progress much further and therefore, the heating was stopped and after 1 h, t-butyl methyl ether (1 L) was added. The mixture was stirred 15 min, then the crystals were filtered and washed with 5 portions of 500 mL of t-butyl methyl ether. The fine white needles were dried at room temperature under vacuum for 24 hours to afford 336.86 g (90% yield) of the title compound: mp 167.5°-168.8° C.; LC-UV-MS analysis: 100% homogeneity (RT=13.4 min) using UV detection at 240 nm and CN column with ACN—$H_2O$ (0.1% formic acid) as gradient eluent; ES(+) m/z 233.2 (M−TsO⁻); ES(−) m/z 171 (TsO⁻). $^1$H NMR ($D_2O$) δ 7.74 (d, 2H), 7.40 (m, 4H), 6.93 (m, 3H), 3.75 (br s, 2H), 3.54 (m, 4H), 3.37 (m, 6H), 2.42 (s, 3H), 2.23 (br s, 2H), 1.32 (t, 6H); $^{13}$C NMR ($D_2O$) δ 6.7, 20.3, 21.5, 42.6, 46.2, 54.5, 59.5, 60.3, 112.8, 117.6, 125.2, 129.0, 129.4, 140.4, 141.2, 147.9. The crude product ASM-024 (222.11 g) was dissolved in hot $CH_2Cl_2$ (750 mL). Then, tBuOMe (160 mL) was added slowly in order to create a mild milky vein and until the appearance of the first crystal, and the mixture was left at room temperature for 3 h. Then, the white solid was filtered, washed with tBuOMe (500 mL) and dried under vacuum. For the second and third recrystallization, the same procedure was used with $CH_2Cl_2$ (750 mL)/tBuOMe (110 mL) and $CH_2Cl_2$ (720 mL)/tBuOMe (120 mL) respectively, to afford 211.7 g of ASM-024 (99% recovery).

EXAMPLE 10

1,1-Diethyl-4-phenyl-homopiperazinium Mesylate (ASM-025)

The resin Amberlite® IRA-400(Cl) (150-170 mL) was treated with 2N HCl (250 mL), and then washed with 250 mL of distilled water. Then the resin was washed with 2N NaOH (250 mL), treated with 2N NaOH (50 mL) in an ultrasonic bath for 20 minutes, washed with 2N NaOH (200 mL). It was washed with a 2N solution of methane sulfonic acid (250 mL), treated with this 2N solution of methane sulfonic acid (50 mL) in an ultrasonic bath for 30 minutes and washed again with this 2N of methane sulfonic acid (200 mL). Finally the resin washed with water (250 mL) and the compound ASM-009 (FG1-60, 2.02 g, 5.61 mmol) was dissolved in $H_2O$ (50 mL) by heating slightly and put down on the resin. The product was eluted with water (500 mL) and the solvent was evaporated and coevaporated with EtOH (3×) to afford the title compound as a white solid (1.707 g): mp=92.8-94.3° C.; $^1$H NMR $D_2O$ (ppm): 7.34 (m, 2H), 6.90 (m, 3H), 3.78 (br s, 2H), 3.55 (m, 4H), 3.39 (m, 6H), 2.78 (s, 3H), 2.31 (br s, 2H), 1.28 (t, 6H); MS ES(+): (M−MsO⁻)=233.2; 100% homogeneity (RT=13.66 min) by LC-MS using CN column with ACN—$H_2O$(0.1% formic acid) as eluent and UV detection at 240 nm; MS ES(−): MsO⁻=95.2.

EXAMPLE 11

1,1-Diethyl-4-phenyl-homopiperazinium Besylate (ASM-033)

To a solution of 1-phenyl-4-ethyl-homopiperazine (6 g, 29.41 mmol) in acetone (30 mL) was added ethyl benzenesulfonate (10.94 g, 58.82 mmol). The mixture was heated gently to reflux temperature for 25 h. The mixture was cooled to room temperature and filtered. The white solid was dried at room temperature under vacuum to afford 10.58 g (92% yield) of the title compound: LC-UV-MS analysis: 100% homogeneity (RT=10.45 min) using UV detection at 240 nm and CN column with ACN—$H_2O$ (0.1% formic acid) as gradient eluent; ES(+) m/z 233.2 (M−$C_6H_5SO_3^-$); ES(−) m/z 157 ($C_6H_5SO_3$); $^1$H NMR $D_2O$ (ppm): 7.79 (dd, 2H), 7.53 (m, 3H), 7.33 (m, 2H), 6.87 (m, 3H), 3.74 (br s, 2H), 3.51 (m, 4H), 3.35 (m, 6H), 2.20 (brs, 2H), 1.26 (t, 6H).

EXAMPLE 12

1,1-Diethyl-4-(2-pyridyl)-homopiperazinium Tosylate (ASM-037)

To a solution of 1-ethyl-4-(2-pyridyl)homopiperazine (1.99 g, 9.7 mmol) in acetone (15 mL) was added ethyl p-toluenesulfonate (3.9 g, 19.4 mmol). The mixture was first stirred at room temperature. After 18 h, the reaction was not complete, then the mixture was heated gently to reflux temperature for 7 h. There was some starting material left, ethyl p-toluenesulfonate (3.9 g, 19.4 mmol) was added and the reaction was stirred for 4 additional days. The mixture was cooled to room temperature and filtered. The white solid was dried at room temperature under vacuum to afford 2.46 g (63% yield) of the title compound: LC-UV-MS analysis: 100% homogeneity (RT=13.70 min) using UV detection at 240 nm and CN column with ACN—$H_2O$ (0.1% formic acid) as gradient eluent; ES(+) m/z 234.2 (M−TsO$^-$); ES(−) m/z 171 (TsO$^-$); $^1$H NMR $D_2O$ (ppm): 8.03 (d, 1H), 7.63 (d, 3H), 7.29 (d, 2H), 6.73 (m, 2H), 3.87 (br s, 2H), 3.60 (t, 2H), 3.50 (m, 2H), 3.32 (m, 6H), 2.32 (s, 3H), 2.20 (br s, 2H), 1.26 (t, 6H).

EXAMPLE 13

1,1-Diethyl-4-(4-chlorophenyl)-homopiperazinium Tosylate (ASM-048)

To a solution of 1-ethyl-4-(4-chlorophenyl)homopiperazine (1.16 g, 4.86 mmol) in acetone (6 mL) was added ethyl p-toluenesulfonate (1.95 g, 9.72 mmol). The mixture was heated gently to reflux temperature for 17 h. The mixture was cooled to room temperature, then t-butyl methyl ether (10 mL) was added. The mixture was stirred 15 min, then filtered and washed with 2 portions of 10 mL of t-butyl methyl ether. The white solid was dried at room temperature under vacuum to afford 2.42 g of the title compound: LC-UV-MS analysis: 73% A, 27% B (LC-UV), 50% A, 50% B (MS), RT=10.62 min (A), 12.05 min (B) using UV detection at 240 nm and CN column with ACN—$H_2O$ (0.1% formic acid) as gradient eluent; ES(+) A m/z 267.2, B m/z 148.2 (M−TsO$^-$); ES(−) m/z 171 (TsO$^-$).

EXAMPLE 14

1,1-Diethyl-4-(4-fluorophenyl)-homopiperazinium Tosylate (ASM-049)

To a solution of 1-ethyl-4-(4-fluorophenyl)homopiperazine (2.27 g, 10.24 mmol) in acetone (12 mL) was added ethyl p-toluenesulfonate (4.1 g, 20.5 mmol). The mixture was heated gently to reflux temperature for 24 h. The mixture was cooled to room temperature, then t-butyl methyl ether (10 mL) was added. The mixture was stirred 15 min, then filtered and washed with 2 portions of 10 mL of t-butyl methyl ether. The white solid was dried at room temperature under vacuum to afford 3.50 g (81% yield) of the title compound: LC-UV-MS analysis: 100% homogeneity (RT=10.43 min) using UV detection at 240 nm and CN column with ACN—$H_2O$ (0.1% formic acid) as gradient eluent; Exact Mass calcd for $C_{15}H_{24}N_2F$ (M$^+$) 251.1915, found 251.1918, $C_7H_7DO_3$ (M$^-$) 171.0117, found 171.0121; mp=169.4-170.5° C.; $^1$H NMR $D_2O$ (ppm): 7.61 (d, 2H), 7.28 (d, 2H), 7.01 (t, 2H), 6.80 (m, 2H), 3.63 (br s, 2H), 3.46 (m, 2H), 3.33 (m, 8H), 2.31 (s, 3H), 2.13 (br s, 2H), 1.22 (t, 6H); $^{13}$C NMR $D_2O$ (ppm): 7.7, 21.2, 22.6, 44.7, 48.5, 55.7, 60.6, 61.5, 115.7, 115.8, 116.4, 116.7, 126.2, 130.1, 141.0, 142.6, 145.8, 145.9, 155.2, 158.3.

EXAMPLE 15

1-Ethyl-1-Methyl-4-(phenyl)-homopiperazinium Tosylate (ASM-055)

To a solution of 1-methyl-4-(phenyl)-homopiperazine (2.13 g, 11.21 mmol) in acetone (14 mL) was added ethyl p-toluenesulfonate (4.5 g, 22.42 mmol). The mixture was heated gently to reflux temperature for 22 h. The mixture was cooled to room temperature, then t-butyl methyl ether (10 mL) was added. The mixture was stirred 15 min, then filtered and washed with 2 portions of 10 mL of t-butyl methyl ether. The white solid was recrystallized twice in dichloromethane/t-butyl methyl ether (40 mL/5 mL), then dried at room temperature under vacuum to afford 3.73 g (85% yield) of the title compound: LC-UV-MS analysis: 100% homogeneity (RT=8.20 min) using UV detection at 240 nm and CN column with ACN—$H_2O$ (0.1% formic acid) as gradient eluent; mp=167.5-168.7° C.; ES(+) m/z 219.2 (M−TsO$^-$); ES(−) m/z 171 (TsO$^-$); $^1$H NMR $D_2O$ (ppm): 7.64 (d, 2H), 7.29 (m, 4H), 6.83 (m, 3H), 3.64 (br s, 2H), 3.29 (m, 8H), 2.94 (s, 3H), 2.32 (s, 3H), 2.13 (br s, 2H), 1.27 (t, 3H); $^{13}$C NMR $D_2O$ (ppm): 6.9, 20.0, 21.6, 42.8, 46.2, 48.0, 59.7, 61.9, 62.3, 112.8, 117.9, 124.9, 129.0, 129.4, 139.2, 141.9, 147.7.

EXAMPLE 16

1,1-Dimethyl-4-(4-methoxyphenyl)-homopiperazinium Tosylate (ASM-057)

To a solution of 4-methyl-1-(4-methoxyphenyl)-homopiperazine (675 mg, 3.07 mmol) in acetone (20 mL) was added methyltosylate (1.143 g, 6.14 mmol). The reaction mixture was stirred at room temperature for 16 h. To precipitate the salt, $Et_2O$ (100 mL) was added to the mixture. After filtration and washing with $Et_2O$, the title compound was obtained as a white solid (1.101 g, 88%): mp 174.0-174.5° C.; LC-UV-MS analysis: >99% homogeneity (RT=10.1 min) using UV detection at 240 nm and CN column with ACN—$H_2O$ (0.1% formic acid) as gradient eluent; $^1$H NMR (400 MHz, $D_2O$) δ 7.66 (d, 2H), 7.31 (d, 2H), 6.94 (d, 2H), 6.86 (d, 2H), 3.76 (s, 3H), 3.63 (m, 2H), 3.57 (m, 2H), 3.49 (m, 2H), 3.42 (m, 2H), 3.12 (s, 6H), 2.34 (s, 3H), 2.19 (m, 2H); $^{13}$C NMR (100 MHz, $CDCl_3$) δ 20.0, 22.0, 44.4, 47.8, 52.6, 52.7, 55.4, 64.7, 114.8, 115.4, 124.9, 129.0, 139.0, 142.0, 142.6, 151.5; ES(−) m/z (p-TsO$^-$) =171.0; Exact Mass Calcd for $C_{14}H_{23}N_2O^+$ [M+H]$^+$ 235.1805, found 235.1796.

EXAMPLE 17

1,1-Dimethyl-4-(4-trifluoromethylphenyl)-homopiperazinium Tosylate (ASM-058)

To a solution of 4-methyl-1-(4-trifluoromethylphenyl)-homopiperazine (593 mg, 2.30 mmol) in acetone (12 mL) was added methyltosylate (857 mg, 4.60 mmol). The reaction mixture was stirred at room temperature for 16 h. To precipitate the salt, $Et_2O$ (100 mL) was added to the mixture. After filtration and washing with $Et_2O$, the title compound was obtained as a white solid (946 mg, 93%): mp 212.6-213.4° C.; LC-UV-MS analysis: >99% homogeneity (RT=10.0 min) using UV detection at 240 nm and CN column with ACN—$H_2O$ (0.1% formic acid) as gradient eluent; $^1$H NMR (400 MHz, MeOD) δ 7.60 (d, 2H), 7.39 (d, 2H), 7.12 (d, 2H), 6.80 (d, 2H), 3.75 (m, 2H), 3.57-3.44 (m, 6H), 3.12 (s, 6H), 2.23 (m, 5H); $^{13}$C NMR (100 MHz, MeOD) δ 21.4, 23.8, 43.7, 47.7, 53.5, 66.4, 66.8, 113.1, 119.1, 120.2, 127.1, 127.8, 130.0, 141.8, 143.8, 152.3; ES(−) m/z (p-TsO$^-$)=171.0; Exact Mass Calcd for $C_{14}H_{20}N_3F_3^+$ [M$^+$] 273.1573, found 273.1577.

EXAMPLE 18

1,1-Dimethyl-4-(4-cyanophenyl)homopiperazinium Tosylate (ASM-064)

To a solution of 4-methyl-1-(4-cyanophenyl)-homopiperazine (915 mg, 4.25 mmol) in a mixture of $Et_2O$/acetone (20 mL/10 mL) was added methyltosylate (1.581 g, 8.50 mmol). The reaction mixture was stirred at room temperature for 24 h. To precipitate the salt, $Et_2O$ (150 mL) was added to the mixture. After filtration and washing with $Et_2O$, the title compound was obtained as a beige solid (1.300 mg, 71%): mp 202.1-203.2° C.; LC-UV-MS analysis: >99% homogeneity (RT=9.1 min) using UV detection at 240 nm and CN column with ACN—$H_2O$ (0.1% formic acid) as gradient eluent; $^1H$ NMR (400 MHz, $D_2O$) δ 7.63 (d, 2H), 7.45 (d, 2H), 7.20 (d, 2H), 6.70 (d, 2H), 3.69 (m, 2H), 3.56 (m, 2H), 3.45 (m, 4H), 3.13 (s, 6H), 2.25 (m, 5H); $^{13}C$ NMR (100 MHz, $D_2O$) δ 20.1, 21.6, 41.7, 45.5, 52.2, 64.4, 64.6, 96.7, 111.5, 120.9, 124.7, 129.0, 133.5, 139.7, 141.5, 150.9; ES(−) m/z (p-TsO$^-$)=171.0; Exact Mass Calcd for $C_{14}H_{20}N_3^+$ [M$^+$] 230.1652, found 230.1648.

EXAMPLE 19

4-Dimethyl-1-(napht-1-yl)-homopiperazinium Tosylate (ASM-067)

To a solution of 4-methyl-1-(napth-1-yl)-homopiperazine (1.17 g, 4.87 mmol) in $Et_2O$ (7 mL) and acetone (2 mL) was added methyltosylate (1.82 g, 9.75 mmol). The reaction mixture was stirred at room temperature for 17 h, filtered and washed with $Et_2O$ to obtain the title compound as a white solid (2.03 g, 98%): mp 177.6-178.8° C.; LC-UV-MS analysis: 100% homogeneity (RT=10.35 min) using UV detection at 240 nm and CN column with ACN—$H_2O$ (0.1% formic acid) as gradient eluent; ES(+) m/z 255.2 (M−TsO$^-$); ES(−) m/z 171 (TsO$^-$). $^1H$ NMR (400 MHz, DMSO) δ 8.16 (d, 1H), 7.91 (d, 1H), 7.65 (d, 1H), 7.50 (m, 5H), 7.23 (d, 1H), 7.10 (d, 2H), 3.82 (m, 2H), 3.76 (m, 2H), 3.52 (br m, 2H), 3.24 (m, 8H), 2.25 (m, 5H); $^{13}C$ NMR (100 MHz, $D_2O$) δ 20.9, 22.9, 48.5, 53.6, 55.4, 64.7, 66.4, 117.0, 123.5, 123.9, 125.6, 125.8, 126.0, 126.1, 128.2, 128.4, 128.6, 134.4, 137.7, 145.8, 149.8; Exact Mass Calcd for [M$^+$] $C_{17}H_{23}N_2$ 255.18558, found 255.1550.

Example 20

4-Dimethyl-1-(3-methylphenyl)-homopiperazinium Tosylate (ASM-068)

To a solution of 4-methyl-1-(3-methylphenyl)-homopiperazine (1.12 g, 5.52 mmol) in $Et_2O$ (7 mL) and acetone (2 mL) was added methyltosylate (2.05 g, 11.04 mmol). The reaction mixture was stirred at room temperature for 21 h, filtered and washed with $Et_2O$ to obtain the title compound as a white solid (1.98 g, 92%): mp 161.6-162.5° C.; LC-UV-MS analysis: 100% homogeneity (RT=10.10 min) using UV detection at 240 nm and CN column with ACN—$H_2O$ (0.1% formic acid) as gradient eluent; ES(+) m/z 219.2 (M−TsO$^-$); ES(−) m/z 171 (TsO$^-$). $^1H$ NMR (400 MHz, $D_2O$) δ 7.55 (d, 2H), 7.20 (d, 2H), 7.12 (t, 1H), 6.56 (m, 3H), 3.58 (br m, 2H), 3.45 (m, 2H), 3.38 (m, 4H), 3.00 (s, 6H), 2.25 (s, 3H), 2.18 (s, 3H), 2.10 (br m, 2H); $^{13}C$ NMR (100 MHz, $D_2O$) δ 20.0, 20.4, 22.0, 42.9, 46.0, 52.2, 52.3, 64.6, 109.7, 113.1, 118.5, 124.9, 129.0, 129.4, 139.1, 139.6, 141.9, 147.8; Exact Mass Calcd for [M$^+$] $C_{14}H_{23}N_2$ 219.18558, found 219.18553.

EXAMPLE 21

4-Dimethyl-1-(napht-2-yl)-homopiperazinium Tosylate (ASM-070)

To a solution of 4-methyl-1-(napht-2-yl)-homopiperazine (1.48 g, 6.17 mmol) in $Et_2O$ (8 mL) was added methyltosylate (2.3 g, 12.34 mmol). The reaction mixture was stirred at room temperature for 18 h, but by MS analysis, there was some starting material left. Then, methyltosylate was added (1.15 g, 6.17 mmol) and the mixture was stirred for 5 h additional, filtered and washed with $Et_2O$ to obtain the title compound as a white solid (2.53 g, 96%): mp 192.6-193.5° C.; LC-UV-MS analysis: >99% homogeneity (RT=10.09 min) using UV detection at 240 nm and CN column with ACN—$H_2O$ (0.1% formic acid) as gradient eluent; ES(+) m/z 255.2 (M−TsO$^-$); ES(−) m/z 171 (TsO$^-$). $^1H$ NMR (400 MHz, DMSO) δ 7.72 (m, 3H), 7.50 (m, 2H), 7.37 (t, 1H), 7.23 (m, 2H), 7.11 (d, 2H), 7.02 (s, 1H), 3.87 (br m, 2H), 3.62 (m, 2H), 3.54 (m, 2H), 3.52 (m, 2H), 3.18 (s, 6H), 2.28 (m, 5H); $^{13}C$ NMR (100 MHz, DMSO) δ 20.9, 22.0, 42.4, 46.9, 52.0, 64.1, 65.1, 105.7, 116.0, 122.1, 125.6, 126.1, 126.3, 126.6, 127.3, 128.2, 128.9, 134.8, 137.7, 145.8, 146.4; Exact Mass Calcd for [M$^+$] $C_{17}H_{23}N_2$ 255.18558, found 255.18558.

EXAMPLE 22

4-Dimethyl-1-(4-trifluorophenyl)-homopiperazinium Iodide (ASM-071)

To a solution of 4-methyl-1-(4-trifluorobenzyl)-homopiperazine (1.5 g, 5.81 mmol) in $Et_2O$ (8 mL) was added iodomethane (1.65 g, 11.63 mmol). The reaction mixture was stirred at room temperature for 24 h, filtered and washed with $Et_2O$ to obtain the title compound as a beige solid (2.32 g, 100%): mp 224.3-225.4° C.; LC-UV-MS analysis: 100% homogeneity (RT=4.83 min) using UV detection at 240 nm and CN column with ACN—$H_2O$ (0.1% formic acid) as gradient eluent; ES(+) m/z 273.0 (M−I$^-$); ES(−) m/z 127.0 (I$^-$). $^1H$ NMR (400 MHz, DMSO) δ 7.50 (d, 2H), 6.92 (d, 2H), 3.87 (br m, 2H), 3.57 (m, 2H), 3.50 (m, 4H), 3.19 (s, 6H), 2.28 (br m, 2H); $^{13}C$ NMR (100 MHz, DMSO) δ 21.6, 41.5, 46.7, 52.0, 64.1, 64.8, 111.7, 115.9, 116.2, 116.5, 116.9, 123.9, 126.3, 126.4, 126.5, 126.6, 151.0; Exact Mass Calcd for [M$^+$] $C_{14}H_{20}F_3N_2$ 273.15731, found 273.15862.

EXAMPLE 23

4-Diethyl-1-(2-pyridyl)-homopiperazinium Iodide (ASM-072)

To a solution of 4-ethyl-1-(2-pyridyl)-homopiperazine (1.81 g, 8.83 mmol) in Acetone (12 mL) was added iodoethane (2.75 g, 17.66 mmol). The reaction mixture was stirred at room temperature for 24 h, filtered and washed with $Et_2O$ to obtain the title compound as a white solid (3.03 g, 95%): mp 166.3-167.2° C.; LC-UV-MS analysis: >99% homogeneity (RT=10.55 min) using UV detection at 240 nm and CN column with ACN—$H_2O$ (0.1% formic acid) as gradient eluent; ES(+) m/z 234.2 (M−I$^-$); ES(−) m/z 127.0 (I$^-$). $^1H$ NMR (400 MHz, $D_2O$) δ 7.92 (m, 1H), 7.52 (m, 1H), 6.64 (m, 2H), 3.79 (br s, 2H), 3.53 (m, 2H), 3.45 (m, 2H), 3.29

(m, 6H), 2.14 (br s, 2H), 1.92 (t, 6H); $^{13}$C NMR (100 MHz, D$_2$O) δ 6.7, 21.3, 40.0, 44.3, 54.3, 59.3, 60.6, 107.0, 112.0, 138.7, 146.5, 156.9; Exact Mass Calcd for [M$^+$] C$_{14}$H$_{24}$N$_3$ 234.19647, found 234.19685.

EXAMPLE 24

1,1-Diethyl-4-(phenyl-4-hydroxy)-homopiperazinium tosylate (ASM-073)

Step 1

To a solution of benzyl 1-homopiperazine carboxylate (5.27 g, 22.5 mmol) in t-BuOH (30 mL) were added EtI (4.2 g, 27 mmol) and Na$_2$CO$_3$ (4.8 g, 45 mmol) at 0° C. Then, the mixture was stirred at reflux temperature for 2.5 h. The volatile was evaporated and the residue was dissolved in H$_2$O and extracted 3 times with Et$_2$O. The organic layer was washed with brine, dried under Na$_2$SO$_4$, filtered and evaporated to afford crude product 1-(Benzylcarboxy)-4-ethyl-homopiperazine (4.95 g, 84% yield) as a orange oil: (M+H)$^+$: 263.6.

Step 2:

To a solution of 1-(benzylcarboxy)-4-ethyl-homopiperazine (4.95 g, 18.89 mmol) in EtOAc (110 mL) was added 10% Pd/C (1 g). The mixture was filled, vented, and filled 3 times with hydrogen and stirred at room temperature under H$_2$ atmosphere for 17 h. The catalyst was filtered on Celite®, washed with EtOAc, and the filtrate and washings were combined and evaporated to provide crude product 1-Ethyl-homopiperazine (2 g, 83% yield) as an oil: 1H NMR (400 MHz, CDCl3) δ 2.90 (m, 4H), 2.59 (m, 6H), 1.73 (m, 3H), 1.04 (m, 3H).

Step 3:

To a solution of 1-ethyl-homopiperazine (740 mg, 5.78 mmol) in toluene (7 mL) were added 4-benzyloxybromobenzene (2 g, 7.51 mmol), KOtBu (8.7 mL, 8.7 mmol), Pd$_2$(dba)$_3$ (264.6 mg, 0.289 mmol) and BINAP (540 mg, 0.867 mmol). The mixture was stirred at 90° C. for 18 h, then cooled down to room temperature. The mixture was diluted with EtOAc (50 mL) and H$_2$O (25 mL). After the separation of the layers, the organic phase was washed once with H$_2$O (25 mL). The combined aqueous phases were back extracted with EtOAc (25 mL). The resulting combined organic phases were extracted with a 2N HCl solution (3×20 mL). The aqueous phases were combined, cooled down with an ice bath and basified up to pH 10 with a 5N NaOH solution. The resulting aqueous phase was extracted with DCM (3×20 mL), washed with brine (25 mL), dried over Na$_2$SO$_4$, filtered, and concentrated under reduced pressure to afford product 1-(phenyl-4-benzyloxy)-4-ethyl-homopiperazine as a brown oil (1.52 g, 85% yield): $^1$H NMR (400 MHz, CDCl$_3$) δ: $^1$H NMR (400 MHz, CDCl$_3$) δ 7.41 (m, 5H), 6.92 (m, 2H), 6.67 (m, 2H), 5.03 (s, 2H), 3.54 (t, 2H), 3.46 (t, 2H), 2.78 (m, 2H), 2.61 (m, 4H), 2.01 (m, 2H), 1.10 (t, 3H); (M+H)$^+$: 311.2.

Step 4:

To a solution of 1-(phenyl-4-benzyloxy)-4-ethyl-homopiperazine (4.51 g, 14.55 mmol) in acetone (20 mL) was added EtOTs (8.73 g, 43.65 mmol). The mixture was stirred at reflux for 41 h, and after cooling down, MTBE (30 mL) was added. After stirring 15 min, the precipitate was filtered and washed with MTBE, dried under vacuum to afford product 1,1-Diethyl-4-(phenyl-4-benzyloxy)-homopiperazinium tosylate (6.88 g, 93%) as a beige solid: $^1$H NMR (400 MHz, CD$_3$OD) δ 7.72 (d, 2H), 7.36 (m, 5H), 7.24 (d, 2H), 6.93 (m, 2H), 6.82 (m, 2H), 5.03 (s, 2H), 3.67 (br s, 2H), 3.61 (m, 2H), 3.46 (m, 8H), 2.38 (s, 3H), 2.23 (br s, 2H), 1.33 (t, 6H); (M)$^+$: 339.3.

Step 5:

To a solution of 1,1-diethyl-4-(phenyl-4-benzyloxy)-homopiperazinium tosylate (6.87 g, 13.47 mmol) in DCM (90 mL) was added 10% Pd/C (700 mg). The mixture was filled, vented, and filled 3 times with hydrogen and stirred at 40° C. under H$_2$ atmosphere for 21 h. The reaction was incomplete by MS analysis, the catalyst was filtered on Celite®, washed with MeOH, and the filtrate and washings were evaporated. The residue was coevaporated with DCM, and dissolved in DCM (90 mL), 10% Pd/C (700 mg) was added, the mixture was filled, vented, and filled 3 times with hydrogen and was heated at 40° C. for an additional 7 h. However, there was some material left, the catalyst was filtered on Celite®, washed with MeOH, and the filtrate and washings were evaporated. The residue was coevaporated with DCM, and dissolved in DCM (90 mL), 10% Pd/C (700 mg) was added. The mixture was filled, vented, and filled 3 times with hydrogen and stirred at 40° C. under H$_2$ atmosphere for an additional 15 h. The catalyst was filtered on Celite®, washed with MeOH, and the filtrate and washings were evaporated. The crude solid was triturated with MTBE and filtered, then triturated 3 times with DCM to afford after drying under vacuum the title compound as a beige solid (4.25 g, 75%): mp=144.0-145.5° C.; $^1$H NMR (400 MHz, CD$_3$OD) δ 7.72 (d, 2H), 7.24 (d, 2H), 6.75 (m, 4H), 3.60 (br s, 4H), 3.45 (m, 8H), 2.38 (s, 3H), 2.20 (br s, 2H), 1.32 (t, 6H); $^{13}$C NMR (100 MHz, CD$_3$OD) δ 7.5, 20.7 23.4, 46.0, 49.9, 55.7, 60.9, 62.6, 116.4, 117.1, 126.4, 129.3, 141.1, 143.1, 143.7, 151.2; HPLC: condition B, RT=5.92 min, 100% homogeneity; ES-MS [p-TsO$^-$]=171.0; Exact Mass Calcd for [M$^+$] C$_{15}$H$_{25}$N$_2$O 249.19614, found 249.19575.

EXAMPLE 25

Cell Proliferation Assay

Figure 1B:
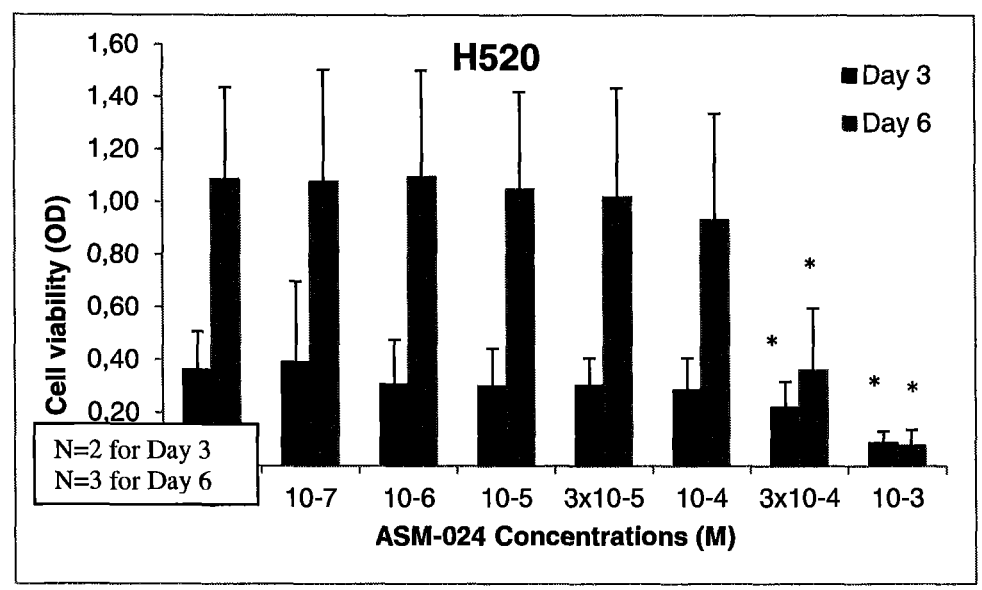
Figure 1C:
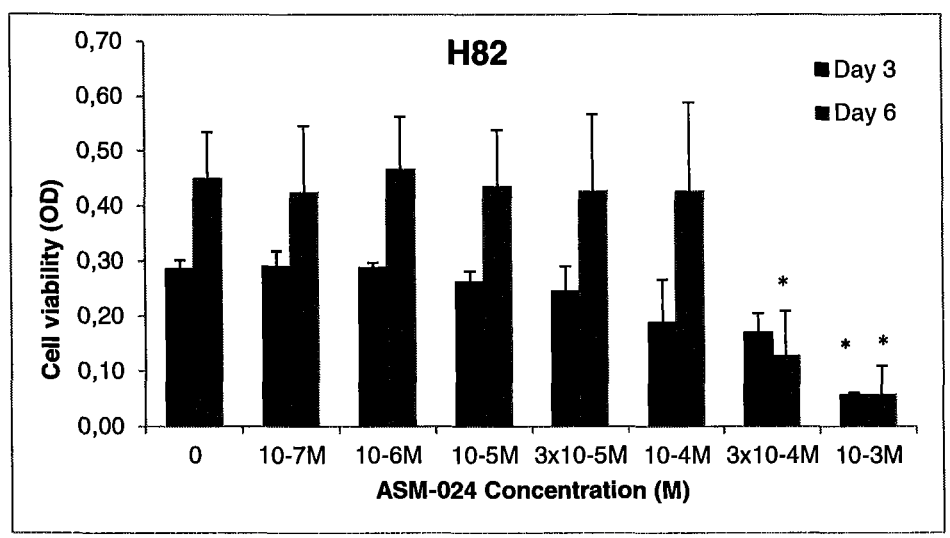
Figure 2A:
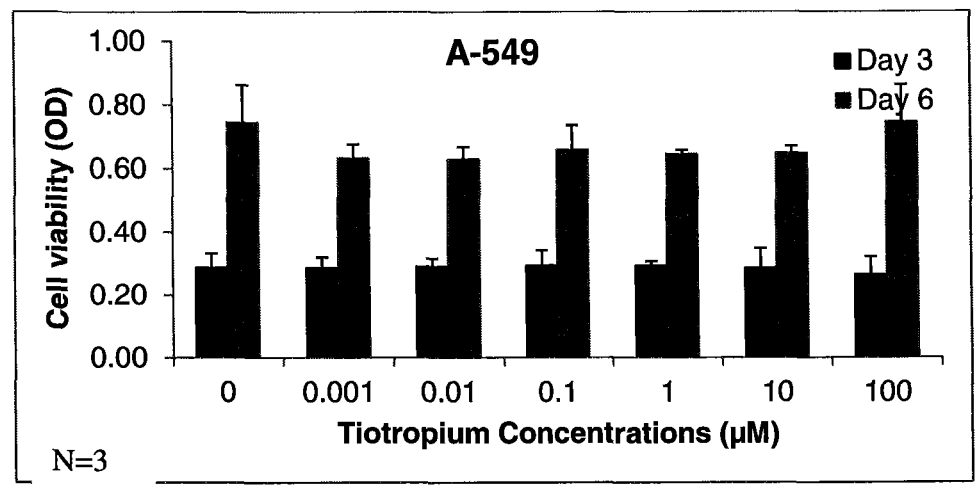
FIGS. 2A-2C show compound-induced dose-related inhibition of A549, H520 and H82 cell proliferation.
Figure 2B:
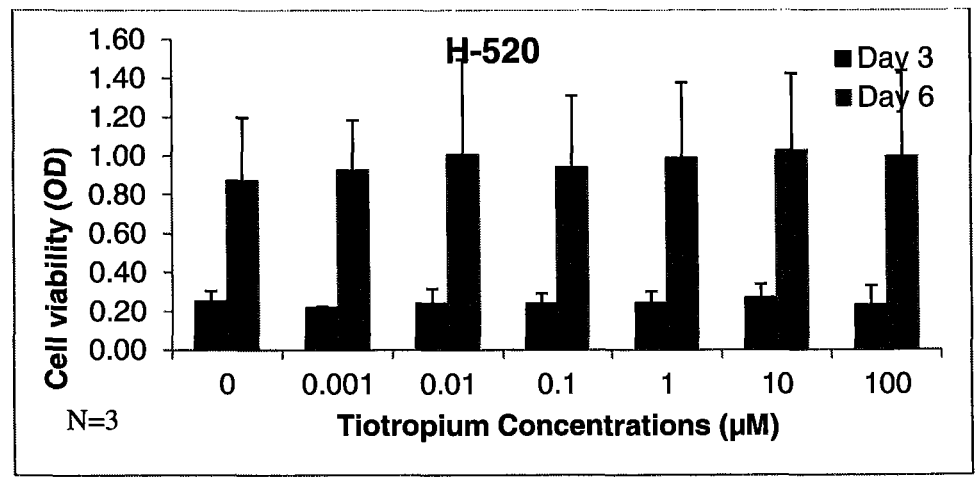
Figure 2C:
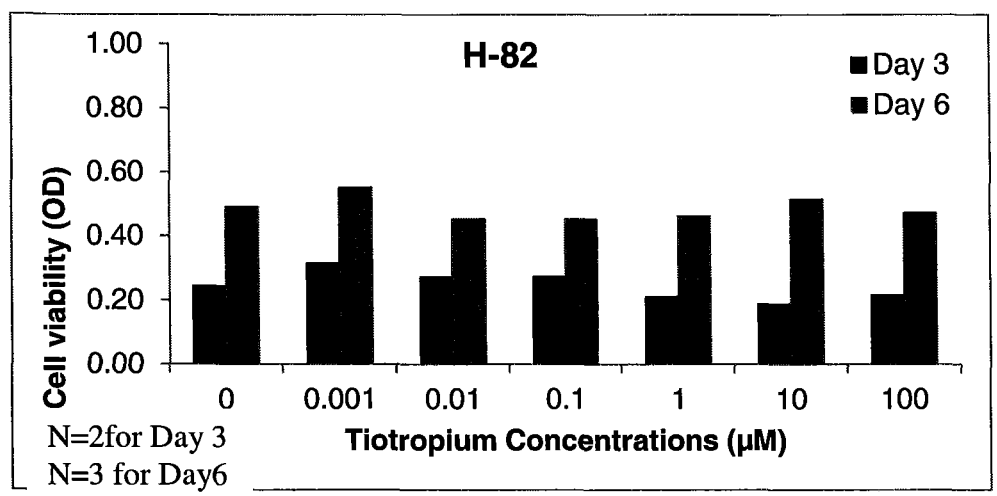
Figure 3A:
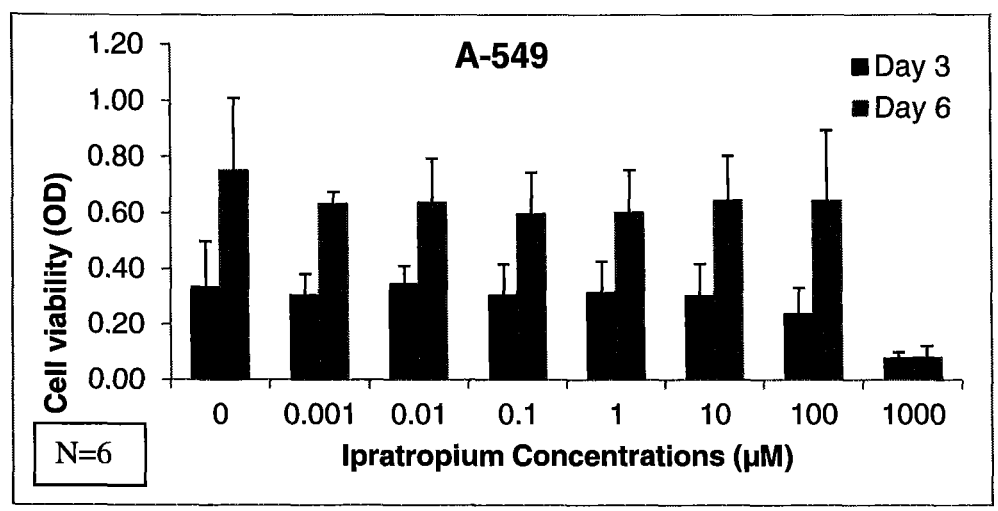
FIGS. 3A-3C show compound-induced dose-related inhibition of A549, H520 and H82 cell proliferation.
Figure 3B:
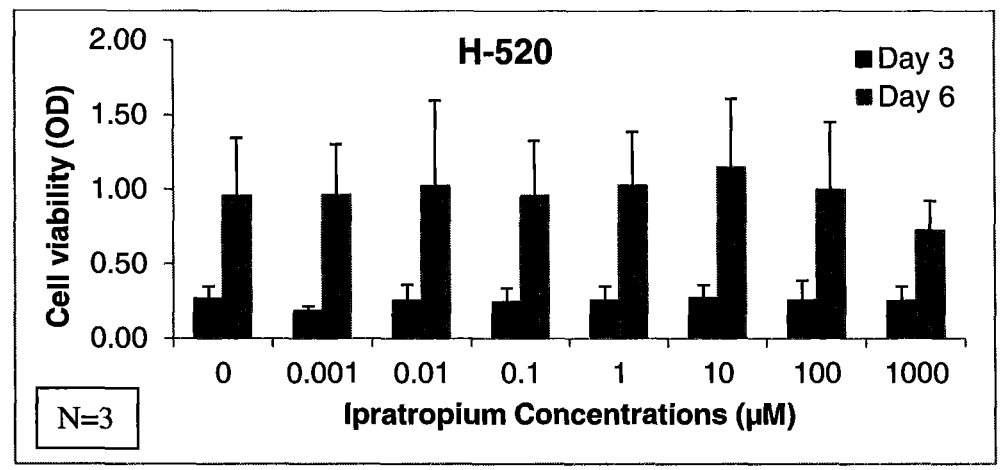
Figure 3C:
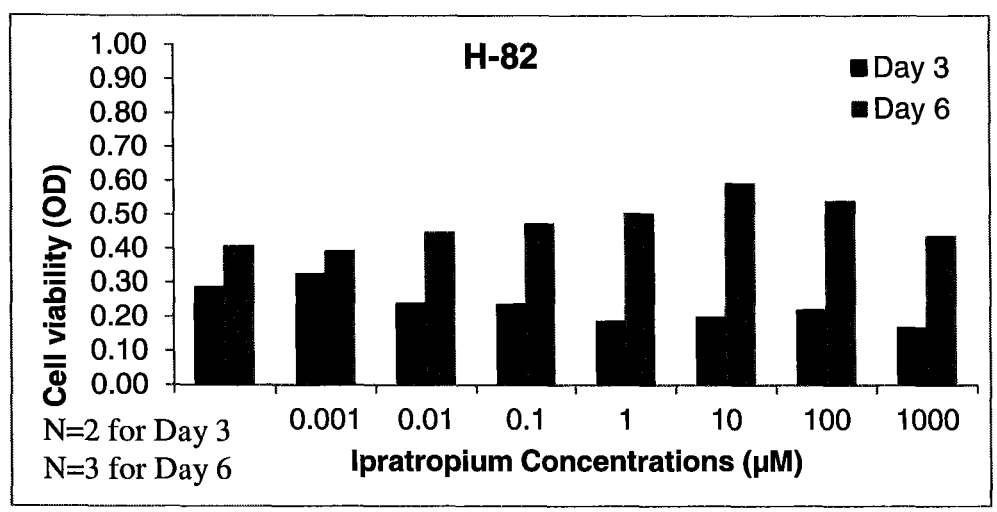
Figure 4A:
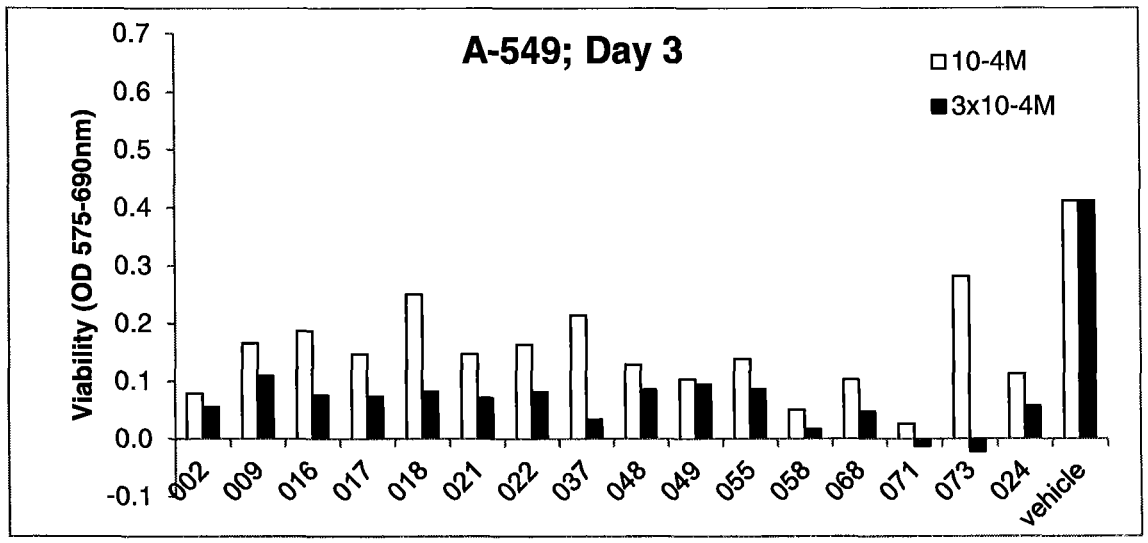
FIGS. 4A-4E show compound-induced dose-related inhibition of A549, H520 and H82 cell proliferation.
Figure 4B:
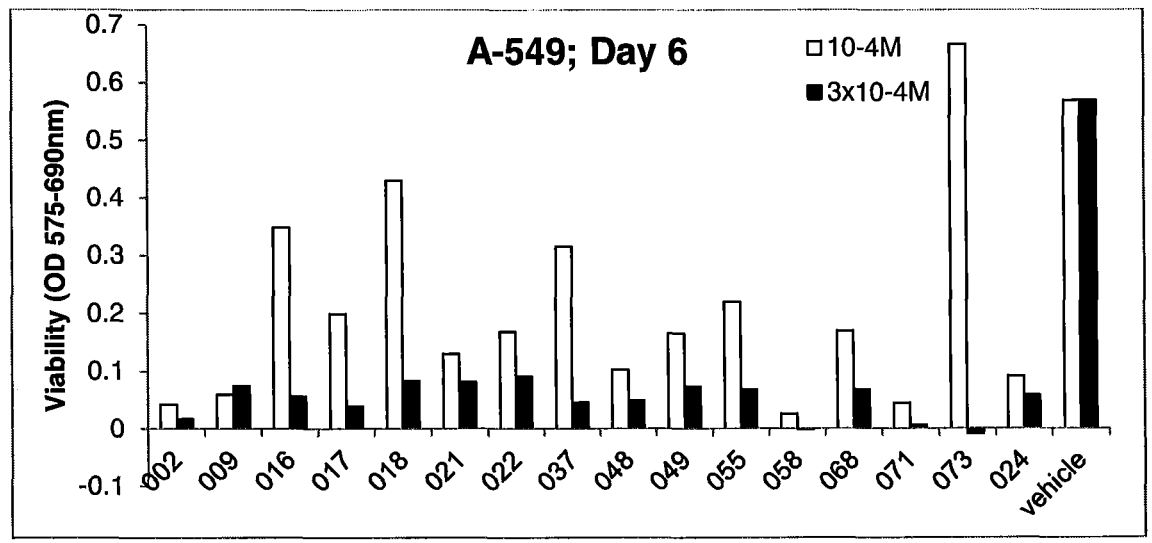
Figure 4C:
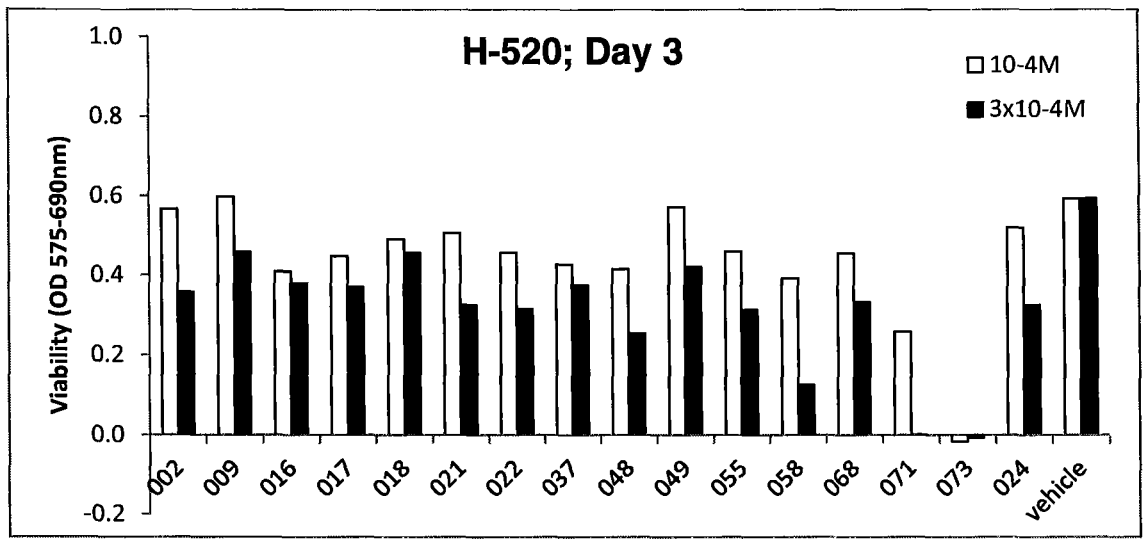
Figure 4D:
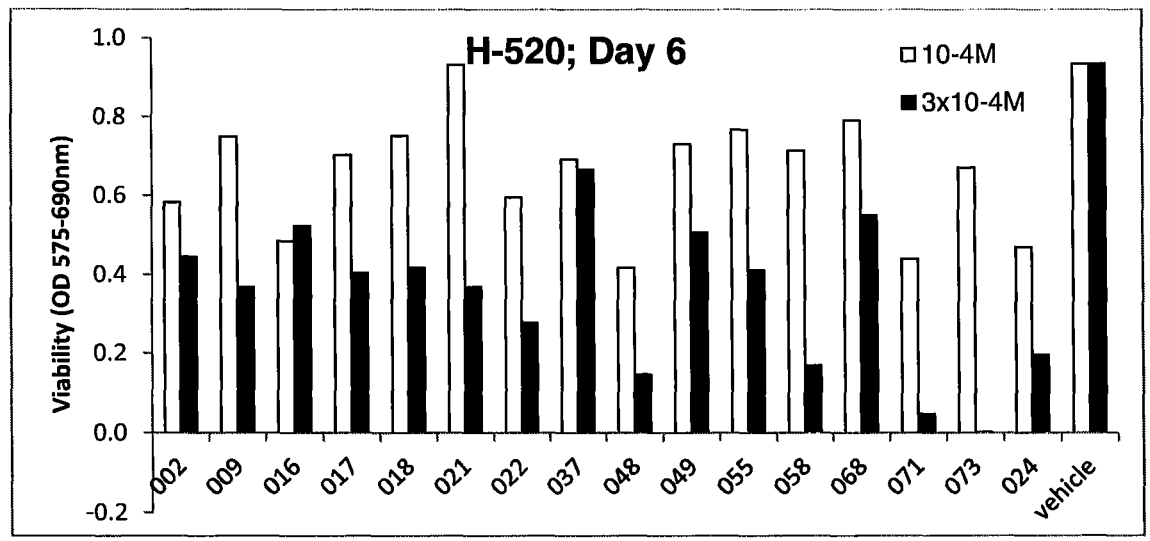
Figure 4E:
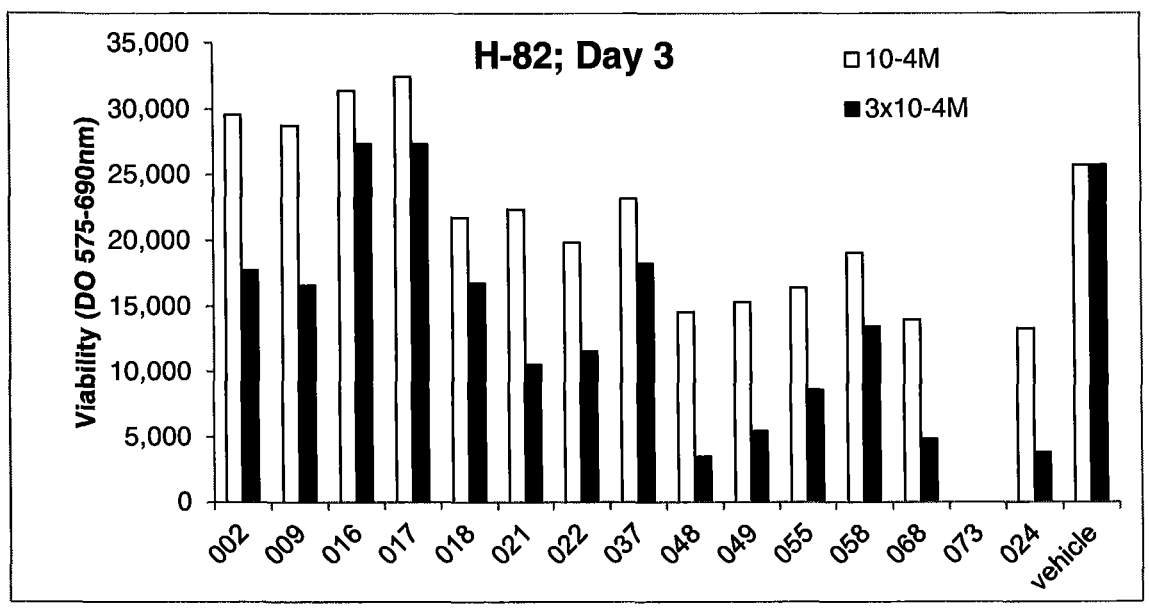

In vitro experiments were conducted on four cancer cell lines: the A549 adenocarcinoma cell line, the H520 squamous cell carcinoma the H82 small cell lung carcinoma and Calu 3 lung adenocarcinoma. The A549 tumor cells, were plated at a density of 1.5×10$^4$ cells per mL and let to adhere on 96-well microplates in F12K cell culture medium enriched with 10% fetal calf serum (FCS). The H520, H82 and Calu 3 tumor cells were plated at a density of 5×10$^4$ cells per mL in RPMI+10% FCS. After 24 h in culture, the medium was changed and cells were exposed to ASM-024 at concentrations ranging from 10$^{-7}$M to 10$^{-3}$M (FIGS. 1A-1C). After 3 and 6 days in culture, cell growth was quantified using the MTT colorimetric assay (M2128, Sigma) at 575-690 nm or the Cell Titer fluorescence assay (G8080, Promega) at 560/590 nm. Tiotropium, a long-acting muscarinic receptor antagonist and ipratropium, a short-acting muscarinic receptor antagonist were tested as well under the same culture conditions at concentrations ranging from (10$^{-9}$ to 10$^{-4}$M) (FIGS. 2A-2C and 3A-3C).

The data illustrated in the figures show a dose-dependent decrease in cell proliferation on day 3 and day 6 by ASM-024 whereas, except for a cytotoxic effect of ipratropium at 1000 μM on A549, no significant cell growth inhibition is observed with either tiotropium and ipratropium.

In an another set of experiments, a series of 16 other homopiperazinium compounds, in addition to ASM-024, were tested for their anti-proliferative effect on the four tumor cell lines described above after up to 6 days in culture at concentrations of 10-7M to 10-3M. (FIGS. 4A-4E) Cell growth was quantified using the MTT colorimetric assay for the A-549, H520 and Calu 3 cell lines and the CellTiter Fluorescence assay.for the H82 tumor cell line These are established method of determining viable cell number in proliferation studies. The preliminary data indicate an inhibitory effect of cell growth for cells exposed to the homopiperazinium compounds compared to vehicle treated cells; this effect appears to be cell line dependant, as well as concentration and time-dependant as a more pronounced inhibition is observed at a higher concentration and after 6 days vs 3 days. in culture. No IC50 could be calculated for Tiotropium

A-549

| Entry | Compound | N | Activity[1] IC$_{50}$ (μM) Day 3 | Day 6 |
|---|---|---|---|---|
| ASM-002 | | 3 | 40 ± 15 | 38 ± 12 |
| ASM-009 | | 3 | 51 ± 6 | 48 ± 25 |
| ASM-016 | | 3 | 90 ± 15 | 58 ± 22 |
| ASM-017 | | 3 | 89 ± 13 | 65 ± 25 |

-continued
| Entry | Compound | N | Activity[1] IC$_{50}$ (μM) Day 3 | Day 6 |
|---|---|---|---|---|
| ASM-018 | 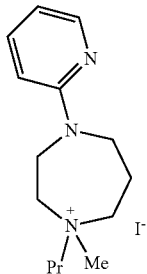 | 3 | 136 ± 39 | 82 ± 32 |
| ASM-021 | 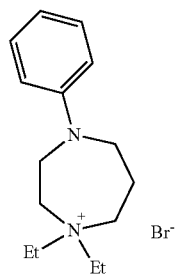 | 3 | 45 ± 12 | 51 ± 39 |
| ASM-022 | 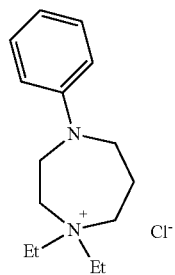 | 3 | 46 ± 7 | 45 ± 32 |
| ASM-024 | 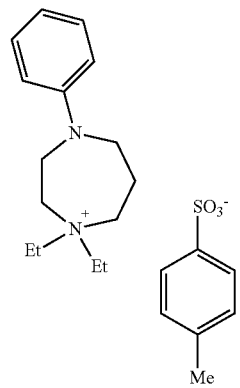 | 10 | 56 ± 20 | 59 ± 21 |
| ASM-037 | 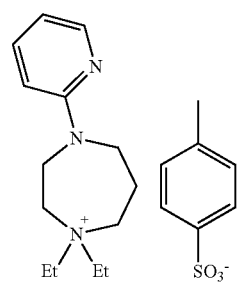 | 3 | 146 ± 92 | 112 ± 96 |

-continued

| Entry | Compound | N | Activity[1] IC$_{50}$ (μM) Day 3 | Day 6 |
|---|---|---|---|---|
| ASM-048 | A, B | 1 | 37 | 15 |
| ASM-049 | | 4 | 81 ± 74 | 42 ± 34 |
| ASM-055 | | 4 | 60 ± 26 | 28 ± 15 |
| ASM-058 | | 5 | 22 ± 10 | 27 ± 26 |

-continued

| Entry | Compound | N | Activity[1] IC$_{50}$ (μM) Day 3 | Day 6 |
|---|---|---|---|---|
| ASM-068 | (3-methylphenyl-diazepane-N,N-dimethyl ammonium, tosylate) | 4 | 36 ± 17 | 20 ± 16 |
| ASM-071 | (4-CF$_3$-phenyl-diazepane-N,N-dimethyl ammonium, iodide) | 3 | 25 ± 15 | 18 ± 9 |
| ASM-073 | (4-OH-phenyl-diazepane-N,N-diethyl ammonium, tosylate) | 3 | 119 ± 49 | 161 ± 82 |

[1]Activity expressed as the drug concentration required to inhibit cell growth by 50%.

H520

| Entry | Compound | N | Activity[1] IC$_{50}$ (μM) Day 3 | Day 6 |
|---|---|---|---|---|
| ASM-002 | (phenyl-diazepane-N,N-dimethyl ammonium, iodide) | 3 | 323 ± 60 | 170 ± 23 |

-continued

| Entry | Compound | N | Activity[1] IC$_{50}$ (μM) Day 3 | Day 6 |
|---|---|---|---|---|
| ASM-009 | | 3 | 892 ± 98 | 396 ± 147 |
| ASM-016 | | 3 | 415 ± 212 | 180 ± 92 |
| ASM-017 | | 3 | 953 ± 39 | 469 ± 163 |
| ASM-018 | | 3 | >1000 | 536 ± 101 |
| ASM-021 | | 3 | >1000 | 369 ± 171 |

-continued

| Entry | Compound | N | Activity[1] IC$_{50}$ (μM) Day 3 | Day 6 |
|---|---|---|---|---|
| ASM-022 | | 3 | >700 | 387 ± 178 |
| ASM-024 | | 8 | 468 ± 287 | 257 ± 257 |
| ASM-037 | | 3 | >1000 | 634 ± 124 |
| ASM-048 | A, B | 1 | 322 | 169 |

-continued

| Entry | Compound | N | Activity[1] IC$_{50}$ (μM) Day 3 | Day 6 |
|---|---|---|---|---|
| ASM-049 | | 4 | >700 | 288 ± 61 |
| ASM-055 | | 4 | 622 ± 211 | 272 ± 65 |
| ASM-058 | | 5 | 356 ± 143 | 210 ± 82 |
| ASM-068 | | 4 | 580 ± 85 | 233 ± 31 |

-continued

| Entry | Compound | N | Activity[1] IC$_{50}$ (μM) Day 3 | Day 6 |
|---|---|---|---|---|
| ASM-071 | [4-(trifluoromethyl)phenyl]-substituted diazepane with N,N,N-trimethyl quaternary ammonium, I⁻ counterion | 3 | 523 ± 292 | 235 ± 179 |
| ASM-073 | [4-hydroxyphenyl]-substituted diazepane with N,N,N-triethyl quaternary ammonium, TsO⁻ counterion | 3 | 187 ± 28 | 148 ± 14 |

[1] Activity expressed as the drug concentration required to inhibit cell growth by 50%.

H82

| Entry | Compound | N | Activity[1] IC$_{50}$ (μM) Day 3 | Day 6 |
|---|---|---|---|---|
| ASM-002 | phenyl-substituted diazepane with N,N-dimethyl quaternary ammonium, I⁻ counterion | | % Inhibition of Cell Growth at day 3 compared to vehicle-treated cells: $10^{-4}$M: −15; $3 \times 10^{-4}$M: 31 | |
| ASM-009 | phenyl-substituted diazepane with N,N-diethyl quaternary ammonium, I⁻ counterion | | % Inhibition of Cell Growth at day 3 compared to vehicle-treated cells: $10^{-4}$M: −12; $3 \times 10^{-4}$M: 35 | |

-continued

| Entry | Compound | N | Activity[1] IC$_{50}$ (μM) Day 3 | Day 6 |
|---|---|---|---|---|
| ASM-016 | | | % Inhibition of Cell Growth at day 3 compared to vehicle-treated cells: $10^{-4}$M: −22; $3 \times 10^{-4}$M: −6 | |
| ASM-017 | | | % Inhibition of Cell Growth at day 3 compared to vehicle-treated cells: $10^{-4}$M: −26; $3 \times 10^{-4}$M: −6 | |
| ASM-018 | | | % Inhibition of Cell Growth at day 3 compared to vehicle-treated cells: $10^{-4}$M: 15; $3 \times 10^{-4}$M: 35 | |
| ASM-021 | | | % Inhibition of Cell Growth at day 3 compared to vehicle-treated cells: $10^{-4}$M: 13; $3 \times 10^{-4}$M: 59 | |
| ASM-022 | | | % Inhibition of Cell Growth at day 3 compared to vehicle-treated cells: $10^{-4}$M: 23; $3 \times 10^{-4}$M: 55 | |

| Entry | Compound | N | Activity[1] IC$_{50}$ (μM) Day 3 | Day 6 |
|---|---|---|---|---|
| ASM-024 | | 3 | 314 ± 205 | 218 ± 76 |
| ASM-037 | | | % Inhibition of Cell Growth at day 3 compared to vehicle-treated cells: $10^{-4}$M: 10; $3 \times 10^{-4}$M: 29 | |
| ASM-048 | A, B | 1 | 246 | 176 |
| ASM-049 | | 1 | 331 | 252 |

| Entry | Compound | N | Activity[1] IC$_{50}$ (μM) Day 3 | Day 6 |
|---|---|---|---|---|
| ASM-055 | [structure: 1-phenyl-4-methyl-4-ethyl-1,4-diazepan-4-ium iodide] | | % Inhibition of Cell Growth at day 3 compared to vehicle-treated cells: $10^{-4}$M: 36; $3 \times 10^{-4}$M: 66 | |
| ASM-058 | [structure: 1-(4-trifluoromethylphenyl)-4,4-dimethyl-1,4-diazepan-4-ium tosylate] | 1 | 472 | 299 |
| ASM-068 | [structure: 1-(3-methylphenyl)-4,4-dimethyl-1,4-diazepan-4-ium tosylate] | 1 | 298 | 179 |
| ASM-073 | [structure: 1-(4-hydroxyphenyl)-4,4-diethyl-1,4-diazepan-4-ium tosylate] | | % Inhibition of Cell Growth at day 3 compared to vehicle-treated cells: $10^{-4}$M: 100; $3 \times 10^{-4}$M: 100 | |

[1] Unless specified otherwise, activity is expressed as the drug concentration required to inhibit cell growth by 50%.

Calu 3

| Entry | Compound | N | Activity[1] IC$_{50}$ (μM) Day 3 | Day 6 |
|---|---|---|---|---|
| ASM-024 | | 2 | 685 ± 320 | 192 ± 217 |
| ASM-048 | A, B | 1 | 276 | 86 |
| ASM-049 | | 1 | 452 | 109 |
| ASM-068 | | 1 | >1000 | 52 |

[1]Activity expressed as the drug concentraion required to inhibit cell growth by 50%.

EXAMPLE 26

In Vitro Anti-Proliferative Properties in other Cancer Cell Lines

The effect of ASM-024 on the growth of MCF7, SK-BR-3, MDA-MB-231, BT-474 (mammary adenocarcinomas), SK-OV/3 (ovary adenocarcinoma), PC3 (prostate adenocarcinoma) SK-MEL-28(skin melanoma) and C6 (tumor cell glioma) was evaluated. Cells were cultured in RPMI medium and incubated with different concentrations of ASM-024. Cell proliferation was measured on days 3 and 6 by the MTT colorimetric assay. Absorbance at 576-690 nm was analyzed with a microplate reader and expressed as optical density (OD) and as a percentage of the value of corresponding untreated cells. The $IC_{50}$ was determined as the drug concentration required to inhibit cell growth by 50% from a plot of percent cell viability from control untreated cells versus treated cells.

Figure 5A:
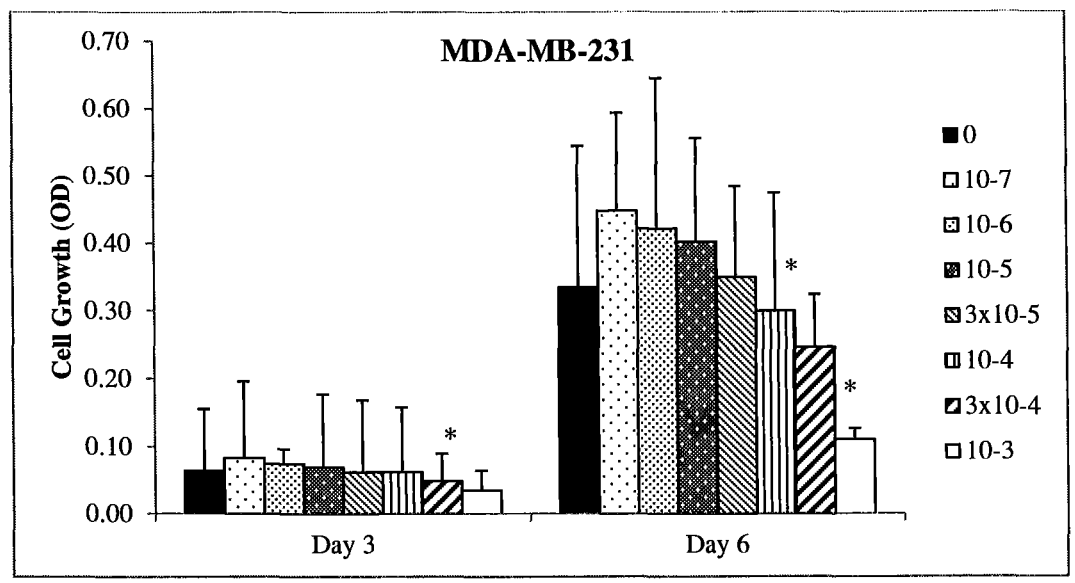
FIGS. 5A and 5B illustrate the observed results for the MDA-MB-231 mammary/breast gland adenocarcinoma assay.
Figure 5B:
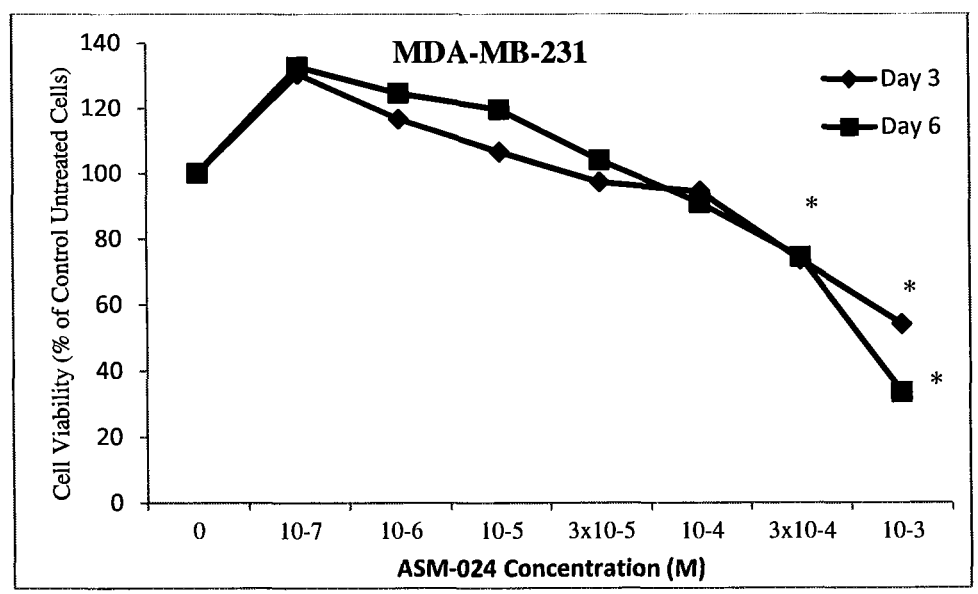

FIGS. 5A and 5B illustrate the observed results for the MDA-MB-231 mammary/breast gland adenocarcinoma assay. Cells were incubated with the dose drug shown and growth measured at the days indicated. In FIG. 5A the data is expressed as optical density (OD) and in FIG. 5B as a percentage of the value of corresponding untreated cells. $P<0.05$ compared to control at same day by Student t-test

| | | $IC_{50}$ | |
|---|---|---|---|
| Cell line | Cancer Type | Day 3 | Day 6 |
| MCF7 | Mammary/breast gland adenocarcinoma | 470 ± 364 | 209 ± 42 |
| SK-BR-3 | Mammary/breast cancer adenocarcinoma | >1000 | 197 ± 67 |
| MDA-MB-231 | Mammary/breast gland adenocarcinoma | >1000 | 661 ± 115 |
| BT-474 | Breast/duct adenocarcinoma | >1000 | 644 ± 230 |
| SK-OV/3 | Ovary adenocarcinoma | >600 | 618 ± 125 |
| SK-MEL-28 | Skin melanoma | >800 | 259 ± 63 |
| C6 | Glioma | 353 ± 52 | 186 ± 27 |
| PC3 | Prostate adenocarcinoma | >700 | 176 ± 29 |

EXAMPLE 27

In Vivo Anti-Tumor Properties

For the in vivo antitumor assay, nu/nu mice were inoculated subcutaneously in the flank of mice with 2×106 A549 cells in sterile PBS mixed with 50% matrigel. Two days later ASM-024 was administered daily by subcutaneous (at a site close to the tumor) or intraperitoneal delivery at the dose of 30 mg/kg for up to 50 days. When palpable, tumor length and width were measured with a caliper and tumor volume calculated according to the formula Volume=(width2× length)/2.

Figure 6A:
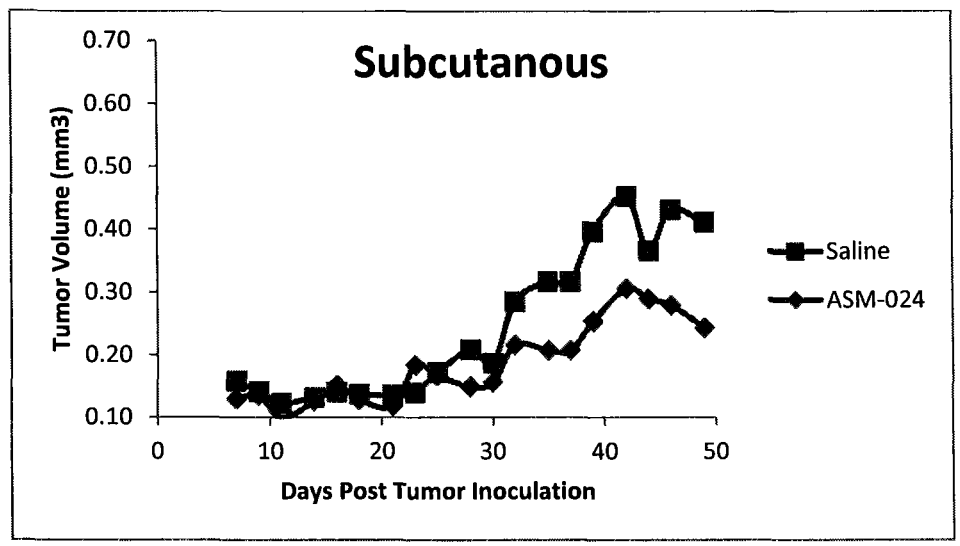
FIGS. 6A and 6B illustrate the antitumor effect of a compound of the invention in A549 tumor cell-bearing mice after 51 days.
Figure 6B:
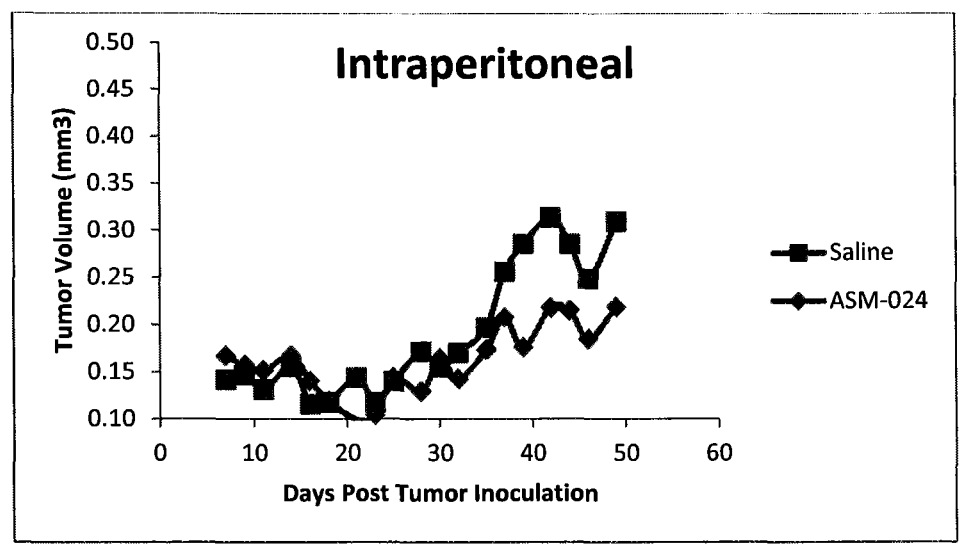
Figure 7A:
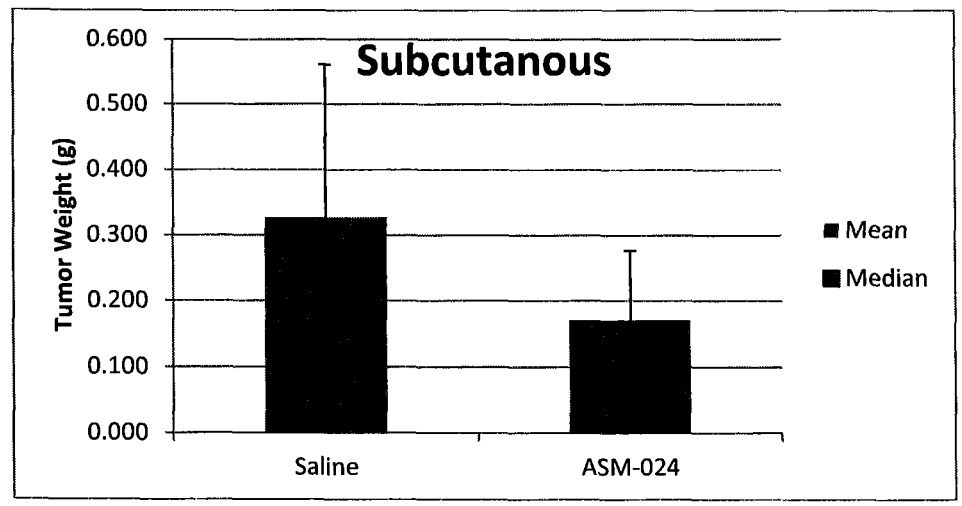
FIGS. 7A and 7B illustrate the antitumor effect of a compound of the invention in A549 tumor cell-bearing mice after 51 days.
Figure 7B:
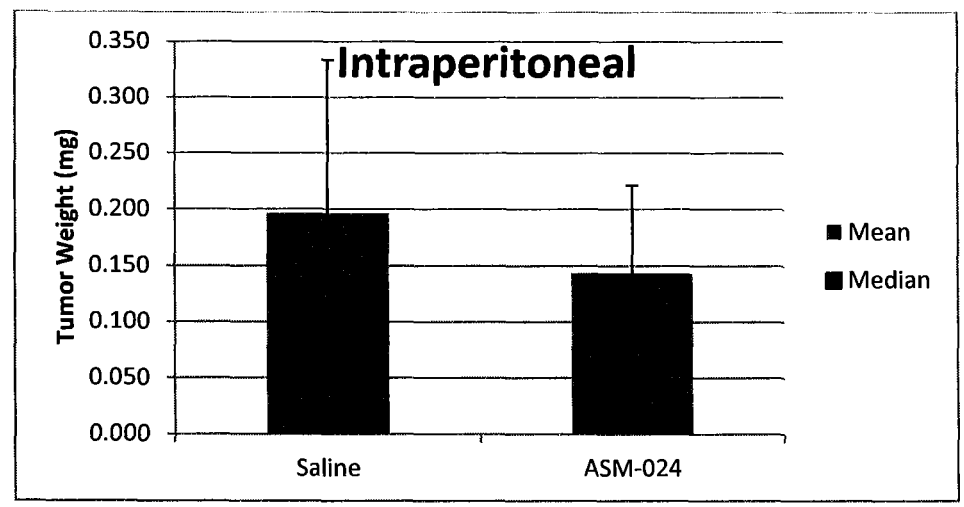

FIGS. 6A, 6B, 7A and 7B are illustrating the antitumor effect of ASM-024 in A549 tumor cell-bearing mice after 51 days. The antitumor effect of each delivery mode was evaluated by measuring tumor volume (FIGS. 6A and 6B) and weight (FIGS. 7A and 7B). Values are presented as the mean±standard deviation.

The in vivo antitumor effects of ASM-024, administered by subcutaneous or intraperitoneal delivery, on A549 cells were investigated in a transplanted tumor nude mice model. Tumor growth, as determined by mean tumor volumes, was reduced after treatment with ASM-024 at a dose of 30 mg/kg during the 51 days of observation, compared to the control mice (FIGS. 6A and 6B). Mean tumor weight after surgical resection also shows a reduction in tumor mass after treatment with ASM-024 compared to vehicle-treated control mice (FIGS. 7A and 7B).

EXAMPLE 28

In Vitro Antitumor Activity of ASM-024-Cisplatin and ASM-024-Taxol Combination Treatments in A549 and MCF7 Cells The concomitant effect of ASM-024 and cisplatin or taxol on the proliferation of A549 lung adenocarcinoma and MCF7 breast cancer adenocarcinoma cells was assessed in vitro.

Method

A549 cells ($3.0\times10^3$ cells/well) were first cultured with 10% FBS in F12K media and MCF7 cells ($10\times10^3$ cells/well) with 10% FBS in EMEM media for 24 hours to allow cells to adhere to the plate at 37° C. in a humidified incubator with 5% CO2. The next day, the media was replaced in medium containing appropriate drug concentrations for two days for an additional 72 hours. Cell viability was quantified using the MTT colorimetric assay (M2128, Sigma) at 575-690 nm.

Results

Figure 8A:
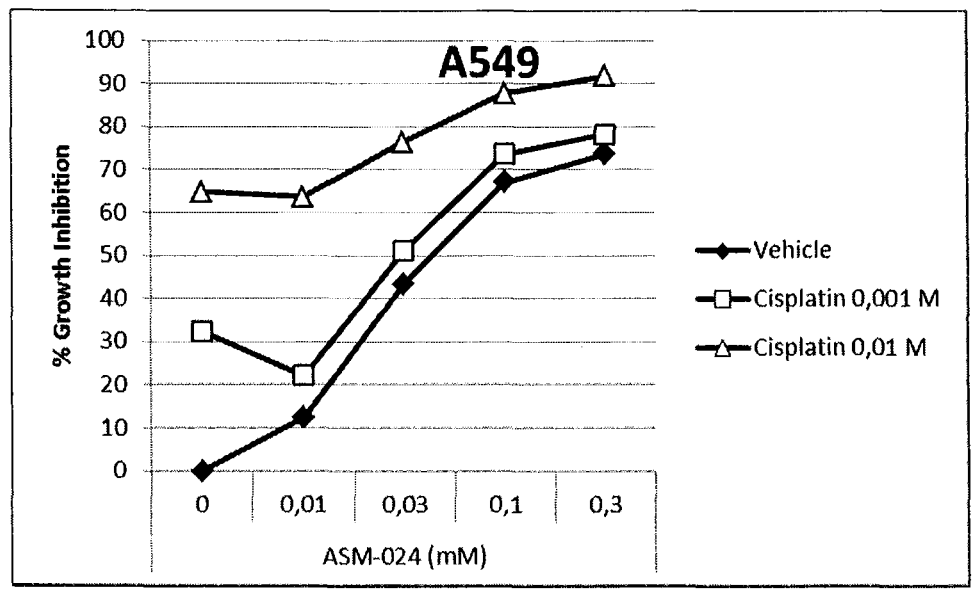
FIGS. 8A and 8B illustrate the in vitro cytotoxicity potentiation of cisplatin and taxol in combination with a compound of the invention in A549 human lung adenocarcinoma.
Figure 8B:
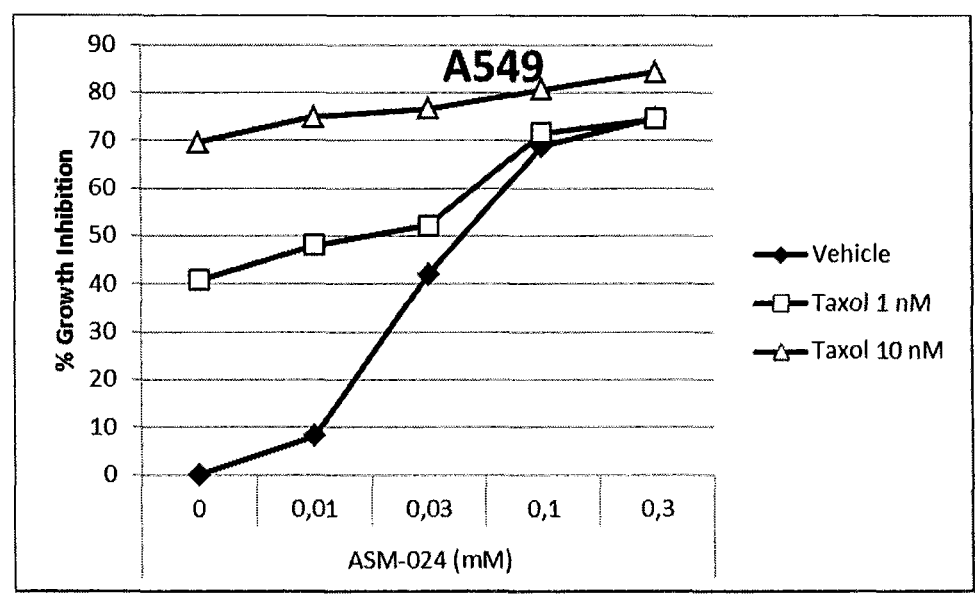

FIG. 8A and FIG. 8B show the percentage of A549 cell growth inhibition after 3 days of drug treatment. ASM-024 induced a dose-dependent growth inhibition of cell proliferation, the concomitant addition of increasing concentrations of Cisplatin (Hospira) or taxol (Paclitaxel, Biolyse Pharma) to suboptimal doses of ASM-024 potentiated the inhibition of in vitro proliferation.

Figure 9A:
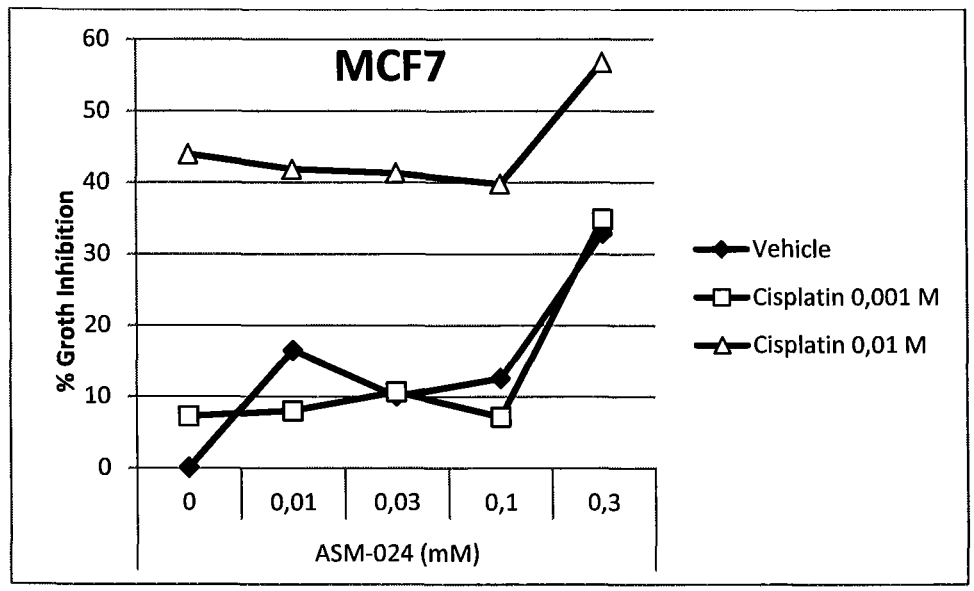
FIGS. 9A and 9B illustrate the in vitro cytotoxicity potentiation of cisplatin or and taxol in combination with a compound of the invention in MCF7 human breast adenocarcinoma.
Figure 9B:
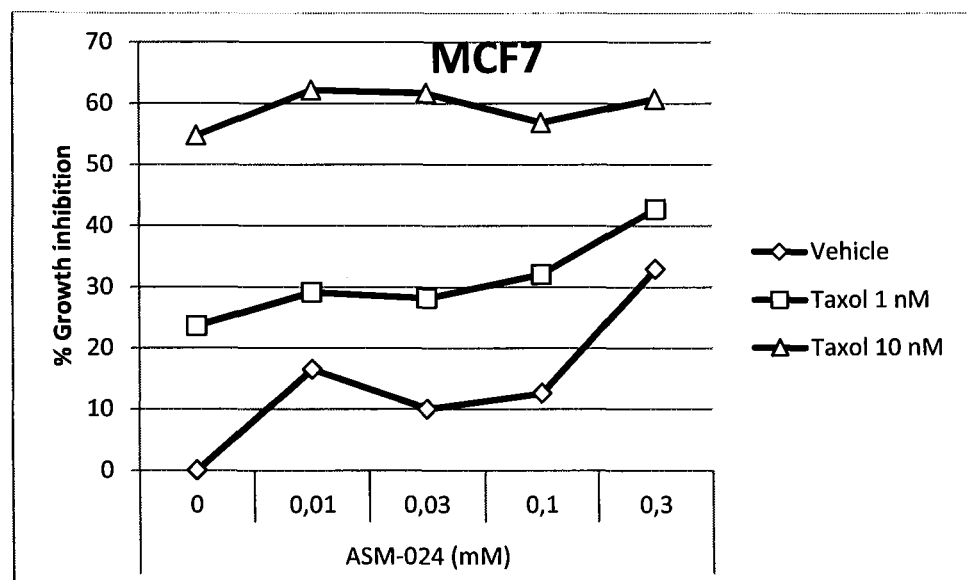

FIG. 9A and FIG. 9B show the percentage of MCF7 cell growth inhibition after 3 days of drug treatment. A similar potentiated inhibition de cell proliferation was observed following combination treatments of ASM-024 and the chemotherapeutic agents.

These results indicate that concomitant treatment with ASM-024 could have clinical applications. ASM-024 may overcome drug resistance to conventional therapeutic doses and thus increase therapeutic efficacy and or allow the administration of lower doses of these drugs thus decreasing their cytotoxicity.

EXAMPLE 29

In Vivo Antitumor Activity of ASM-024, Compared to Cisplatin and Taxol Treatments in Xenografts Models of Human Lung and Breast Cancers Method For the in vivo antitumor assay, A549 human lung carcinoma cells (3.5×106) in 50% F12K medium (Matrigel) were implanted subcutaneously in the flank of Balb/c nude mice (nu/nu, Charles River) and allowed to grow for 14 days. ASM-024 was administered daily by subcutaneous delivery at the dose of 45 mg/kg from day 14 to day 38 post cell inoculation. Taxol was administrated intraperitoneally at the dose of 10 mg/kg on days 21, 28 and 35. Cisplatin was administrated intraperioneally at the dose of 2.5 mg/kg on days 28 and 35. From day 14 to day 49, tumor length and width were measured once or twice a week with a caliper and tumor volume calculated according to the formula Volume=(width2×length)/2.

Results

Figure 10A:
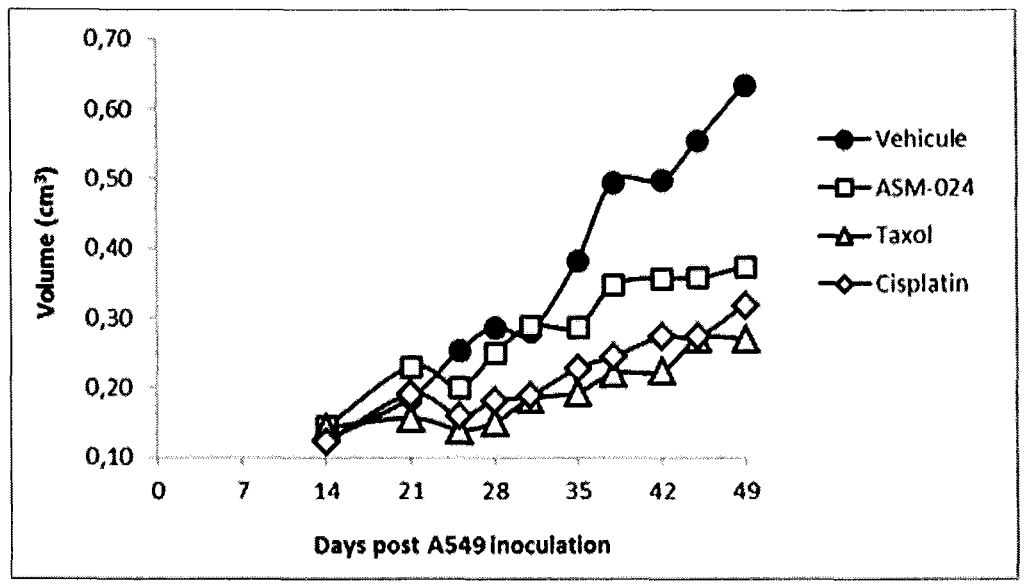
FIGS. 10A and 10B represent the tumor volume in nude mice treated with either cisplatin, taxol or a compound of the invention.
Figure 10B:
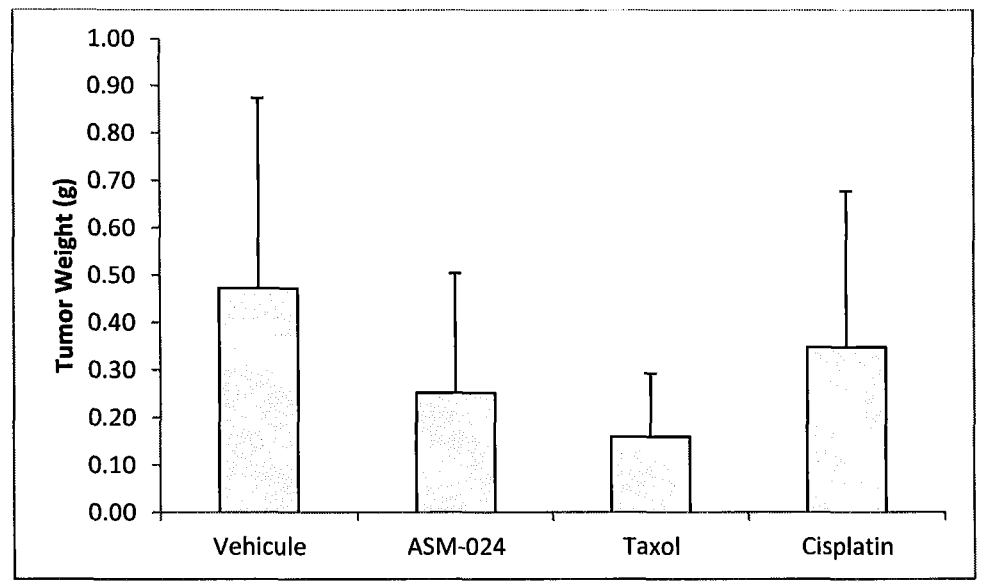

After 49 days of treatment, a decrease in A549 human carcinoma tumor growth is observed in cisplatin, taxol or ASM-024 treated mice (see FIGS. 10A and 10B).

While the invention has been described in connection with specific embodiments thereof, it is understood that it is capable of further modifications and that this application is intended to cover any variation, use, or adaptation of the invention following, in general, the principles of the invention and including such departures from the present disclosure that come within known, or customary practice within the art to which the invention pertains and as may be applied to the essential features hereinbefore set forth, and as follows in the scope of the appended claims. All references cited herein are incorporated by reference in their entirety.

The invention claimed is:

1. A method for treating cancer comprising administering to a patient in need thereof an effective amount of a compound having the formula:

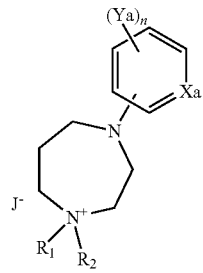

wherein $R_1$ and $R_2$ are independently alkyl of 1 to 6 carbon atoms or cycloalkyl of 3 to 6 carbon atoms, Xa is CH or N, Ya is hydrogen or independently selected from halogen, cyano, hydroxyl, alkyl of 1 to 6 carbon atoms, alkoxy of 1 to 6 carbon atoms, heteroaryl of 6 members and aryl, n is an integer from 1 to 5, J is a counter ion; and wherein said cancer is a carcinoma or a blastoma, wherein said carcinoma is selected from the group of lung cancer and colon cancer, and wherein said blastoma is a neuroblastoma.

2. The method as defined in claim 1, wherein $R_1$ and $R_2$ are independently selected from methyl, ethyl, n-propyl, or i-propyl.

3. The method as defined in claim 1, wherein Xa is CH.

4. The method as defined in claim 1, wherein Xa is N.

5. The method as defined in claim 1, wherein n is 1 or 2.

6. The method as defined in claim 1, wherein R1 and R2 are independently selected from methyl, ethyl, n-propyl, or i-propyl;

Xa is N or CH;

Ya is hydrogen or independently selected from halogen, cyano, hydroxyl, alkyl of 1 to 6 carbon atoms, alkoxy of 1 to 6 carbon atoms, heteroaryl of 6 members and aryl;

n is 1 or 2;

wherein J⁻ is fluoride, chloride, bromide, iodide, acetate, sulfate or sulfonate.

7. The method as defined in claim 1, wherein R1 and R2 are independently selected from methyl, ethyl, n-propyl, or i-propyl;

Xa is CH;

Ya is hydrogen or independently selected from halogen, cyano, hydroxyl, alkyl of 1 to 6 carbon atoms, alkoxy of 1 to 6 carbon atoms, heteroaryl of 6 members and aryl;

n is 1;

wherein J⁻ is fluoride, chloride, bromide, iodide, acetate, sulfate or sulfonate.

8. The method as defined in claim 6, wherein said sulfonate is tosylate, mesylate or besylate.

9. The method as defined in claim 7, wherein said sulfonate is tosylate, mesylate or besylate.

10. The method as defined in claim 1, wherein said compound has the formula:

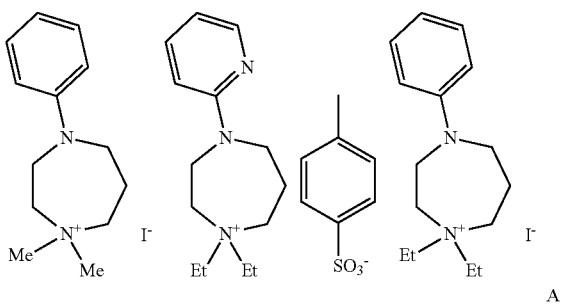

A

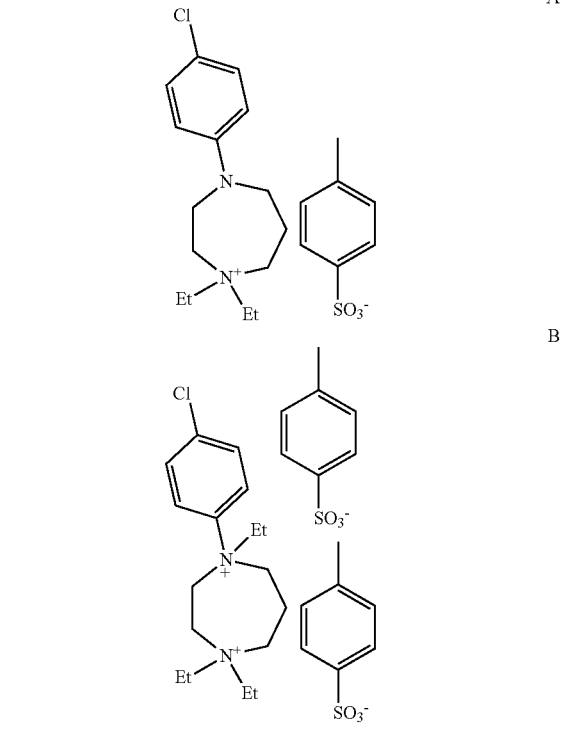

B

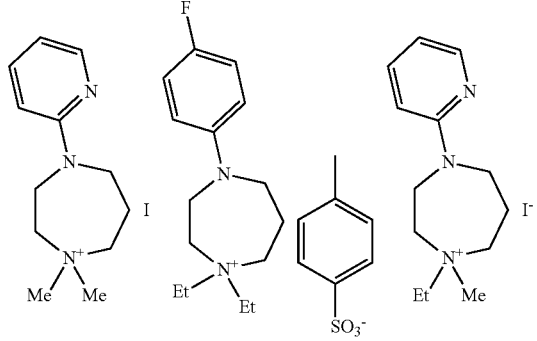

-continued

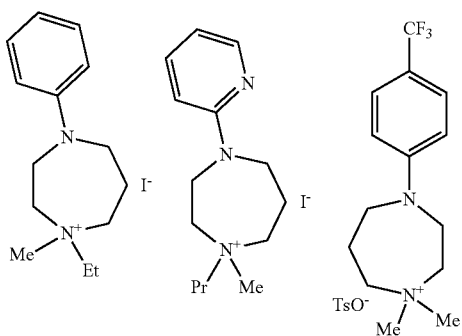

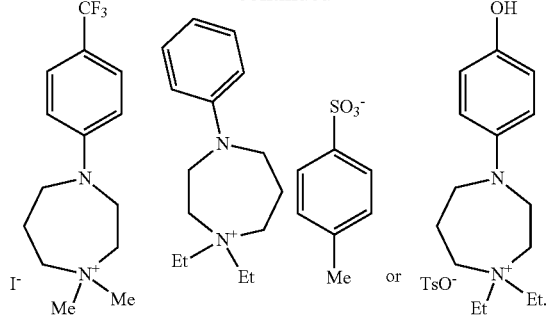

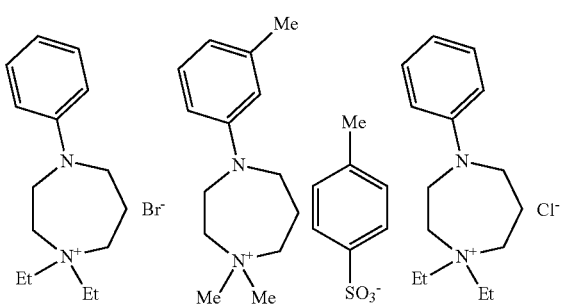

11. The method as defined in claim 1, wherein said cancer is a cancer of the colon.

12. The method as defined in claim 1, wherein said cancer is neuroblastoma.

13. The method as defined in claim 1, further comprising administering a therapeutically effective amount of at least one or more therapeutic agents selected from: Alkylating agents, anti-metabolites, plant alkaloids and terpenoids, vinca alkaloids, podophyllotoxin, taxanes, topoisomerase inhibitors, and cytotoxic antibiotics.

14. The method as defined in claim 1, further comprising administering a therapeutically effective amount of at least one or more therapeutic agents selected from imatinib, paclitaxel, docetaxel, cisplatin, doxorubicine, vinblastine, zoledronate, avastatin, Velcade, arimidex, tamoxifen, bicalutamide, trastuzumab, and vemurafenib.

* * * * *